(12) United States Patent
Zohar et al.

(10) Patent No.: US 9,974,832 B2
(45) Date of Patent: *May 22, 2018

(54) THERAPEUTIC EFFECTS OF BRYOSTATINS, BRYOLOGS, AND OTHER RELATED SUBSTANCES ON HEAD TRAUMA-INDUCED MEMORY IMPAIRMENT AND BRAIN INJURY

(75) Inventors: Ofer Zohar, Gaithersburg, MD (US); Daniel L. Alkon, Bethesda, MD (US)

(73) Assignee: Cognitive Research Enterprises, Inc., Morgantown, WV (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/068,742

(22) Filed: Feb. 11, 2008

(65) Prior Publication Data

US 2008/0207742 A1    Aug. 28, 2008

Related U.S. Application Data

(60) Provisional application No. 60/900,338, filed on Feb. 9, 2007, provisional application No. 60/924,663, filed on May 24, 2007.

(51) Int. Cl.
*A61K 31/366* (2006.01)
*A61K 31/192* (2006.01)
(Continued)

(52) U.S. Cl.
CPC .......... *A61K 38/1825* (2013.01); *A61K 31/00* (2013.01); *A61K 31/05* (2013.01);
(Continued)

(58) Field of Classification Search
None
See application file for complete search history.

(56) References Cited

U.S. PATENT DOCUMENTS 4,560,774 A   12/1985   Pettit et al.
4,611,066 A    9/1986   Pettit et al.
(Continued)

FOREIGN PATENT DOCUMENTS

CA   2401452    3/2003
DE   A-3827974  2/1990
(Continued)

OTHER PUBLICATIONS

Wang et al. Neuroprotection targets after traumatic brain injury. Curr. Op. Neur. 19, 514-519 (2006).*

(Continued)

*Primary Examiner* — Jianfeng Song
(74) *Attorney, Agent, or Firm* — Finnegan, Henderson, Farabow, Garrett & Dunner, LLP

(57) ABSTRACT

The invention provides for the use of protein kinase activators or boosters of nerve growth factor (NGF), brain-derived neurotrophic factor (BDNF) or other neurotrophic factors to treat head trauma. Specifically, the present invention provides methods of treating head trauma comprising the steps of identifying a subject having suffered a head trauma and administering to said subject an amount of a pharmaceutical composition comprising a protein kinase C (PKC) activator or 4-methylcatechol acetic acid (MCBA) and a pharmaceutically acceptable carrier effective to treat at least one symptom of head trauma.

12 Claims, 3 Drawing Sheets

(51) Int. Cl.

| | | |
|---|---|---|
| A61K 38/18 | (2006.01) | |
| A61K 31/00 | (2006.01) | |
| A61K 31/05 | (2006.01) | |
| A61K 31/335 | (2006.01) | |
| A61K 31/35 | (2006.01) | |
| A61K 31/365 | (2006.01) | |
| A61K 31/395 | (2006.01) | |
| A61K 31/4015 | (2006.01) | |
| A61K 38/00 | (2006.01) | |

(52) U.S. Cl.
CPC ............ *A61K 31/335* (2013.01); *A61K 31/35* (2013.01); *A61K 31/365* (2013.01); *A61K 31/395* (2013.01); *A61K 31/4015* (2013.01); *A61K 38/00* (2013.01)

(56) References Cited

U.S. PATENT DOCUMENTS

| | | | |
|---|---|---|---|
| 4,833,139 | A | 5/1989 | Martin |
| 4,833,257 | A | 5/1989 | Pettit et al. |
| 5,072,004 | A | 12/1991 | Pettit |
| 5,196,447 | A | 3/1993 | Pettit et al. |
| 5,288,514 | A | 2/1994 | Ellman |
| 5,359,115 | A | 10/1994 | Campbell et al. |
| 5,362,899 | A | 11/1994 | Campbell |
| 5,393,897 | A | 2/1995 | Pettit et al. |
| 5,430,053 | A | 7/1995 | Pettit et al. |
| 5,545,636 | A | 8/1996 | Heath et al. |
| 5,578,590 | A | 11/1996 | Grunicke et al. |
| 5,580,748 | A | 12/1996 | Alkon et al. |
| 5,625,232 | A | 4/1997 | Numata et al. |
| 5,770,593 | A | 6/1998 | Grunicke et al. |
| 5,891,870 | A | 4/1999 | Driedger et al. |
| 5,891,906 | A | 4/1999 | Driedger et al. |
| 5,955,501 | A | 9/1999 | Driedger et al. |
| 5,962,498 | A | 10/1999 | Driedger et al. |
| 5,962,504 | A | 10/1999 | Kozikowski et al. |
| 5,981,165 | A | 11/1999 | Weiss et al. |
| 6,043,270 | A | 3/2000 | Driedger et al. |
| 6,080,582 | A | 6/2000 | Alkon et al. |
| 6,080,784 | A | 6/2000 | Driedger et al. |
| 6,187,568 | B1 | 2/2001 | Nishida et al. |
| 6,242,479 | B1 | 6/2001 | Wechter |
| 6,407,058 | B1 | 6/2002 | Staddon et al. |
| 6,458,373 | B1 | 10/2002 | Lambert et al. |
| 6,624,189 | B2 | 9/2003 | Wender et al. |
| 6,825,229 | B2 | 11/2004 | Etcheberrigaray et al. |
| 7,803,400 | B2 | 9/2010 | Nelson et al. |
| 7,977,377 | B2 | 7/2011 | Sun et al. |
| 2002/0193360 | A1 | 12/2002 | Villalobos |
| 2003/0050302 | A1 | 3/2003 | Etcheberrigaray |
| 2003/0077335 | A1 | 4/2003 | Richardson et al. |
| 2003/0171356 | A1 | 9/2003 | Etcheberrigaray et al. |
| 2003/0171385 | A1 | 9/2003 | Alkon et al. |
| 2005/0037984 | A1 | 2/2005 | Etcheberrigaray et al. |
| 2005/0065205 | A1 | 3/2005 | Alkon |
| 2005/0075393 | A1 | 4/2005 | Nishizaki et al. |

FOREIGN PATENT DOCUMENTS

| | | | |
|---|---|---|---|
| DE | 19943198 | 3/2001 | |
| EP | 0 115 472 | 8/1984 | |
| EP | 0 324 574 | 7/1989 | |
| EP | 0 413 191 | 2/1991 | |
| EP | 0 432 856 | 6/1991 | |
| EP | 1 195 159 | 4/2002 | |
| JP | 06-279311 | 10/1994 | |
| JP | 2001-240581 | 9/2001 | |
| JP | 2003-146883 | 5/2003 | |
| WO | WO 92/10092 | 6/1992 | |
| WO | WO 93/09668 | 5/1993 | |
| WO | WO 93/20242 | 10/1993 | |
| WO | WO 94/08051 | 4/1994 | |
| WO | WO 96/35417 | 11/1996 | |
| WO | WO 97/43268 | 11/1997 | |
| WO | WO 98/32464 | 7/1998 | |
| WO | WO 99/59597 | 11/1999 | |
| WO | WO01/68137 | * 9/2001 | ............ A61K 45/00 |
| WO | WO 2001/83449 | 11/2001 | |
| WO | WO 2001/93883 | 12/2001 | |
| WO | WO 2002/50013 | 6/2002 | |
| WO | WO 2002/083877 | 10/2002 | |
| WO | WO 2002/086106 | 10/2002 | |
| WO | WO 2002/087423 A3 | 11/2002 | |
| WO | WO 03/075850 A2 | 9/2003 | |
| WO | WO 2003/075850 | 9/2003 | |
| WO | WO 2003/075930 | 9/2003 | |
| WO | 2004004641 | 1/2004 | |
| WO | WO-2004-004641 | * 1/2004 | |
| WO | 2004047857 | 6/2004 | |
| WO | WO 91/07087 | 4/2005 | |
| WO | WO 2005/032474 | 4/2005 | |
| WO | WO 2005/115548 | 12/2005 | |
| WO | 200603137 | 3/2006 | |
| WO | WO 2006/031337 | 3/2006 | |
| WO | WO 2007/016202 | 2/2007 | |
| WO | WO 2007/044094 | 4/2007 | |
| WO | 2008013573 | 1/2008 | |
| WO | 2008/100449 | 8/2008 | |

OTHER PUBLICATIONS

Tenovuo, O. Pharmacological enhancement of cognitive and behavioral deficits after traumatic brain injury. Curr. Op. Neur. 19, 528-533 (2006).*
Etcheberrigaray et al. Therapeutic effects of PKC activators in Alzheimer's disease transgenic mice. PNAS 101(30), 11141-46 (2004).*
Paul A. Wender, et al, Function Oriented Synthesis: The design, Synthesis, PCK Binding and Translocation Activity of a New Bryostatin Analog, 1 Curr. Drug Disc. Tech. 1 (2004).*
Paul A. Wender, et al, Total Synthesis and Initial Biological Evaluation of New B-Ring-Modified Bryostatin Analogs, 8 Org. Lett. 5299 (Oct. 20, 2006).*
Paul A. Wender, et al, The Design, Computer Modeling, Solution Structure, and Biological Evaluation of Synthetic Analogs of Bryostatin I, 95 Proc. Natl. Acad. Sci. 6624 (Jun. 1998)).*
International Search Report and Written Opinion for PCT/US2008/006158 dated Apr. 9, 2009.
Alkon et al., Protein Synthesis Required for Long-Term Memory is Induced by PKC Activation on Days Before Associative Learning, Proc. Natl. Acad. Sci. USA,102:16432-16437 (2005).
Alkon, D.L., "Calcium-mediated reduction of ionic currents: A biophysical memory trace." Science, vol. 226, pp. 1037-1045, 1984.
Bondy et al., "The PHA-Induced Calcium Signal in Lymphocytes is Altered After Blockade of K+-Channels in Alzheimer's Disease," J. Psychiat. Res., 30(3):217-227 (1996).
Burke et al., "Update on Alzheimer's Disease: Promising advances in Detection and Treatment," Postgraduate Medicine, 106(5): 85-95 (1999).
Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).
Certified U.S. Appl. No. 60/392,951, filed 2002.
Espacenet English Abstract for EP 0 115 472, (2012).
English-language Translation for JP 6-279311, dated Jun. 2008.
English-language Translation for JP 2001-240581 (2012).
Espacenet English Abstract for JP 2003-146883 (2012).
Connolly, "Fibroblast Models of Neurological Disorders: Fluorescence Measurement Studies," TIPS, 19:171-177 (1998).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Favit et al., "Alzheimer's-specific effects of soluble β-amyloid on protein kinase C-α and -γ degradation in human fibroblasts", Cell Biology, 95:5562-5567 (1998).

(56) References Cited

OTHER PUBLICATIONS

Final Office Action dated Nov. 23, 2010, in U.S. Appl. No. 11/802,842.
Final Office Action dated Mar. 5, 2009, in U.S. Appl. No. 10/933,536.
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Govoni et al., "Cytosol Protein Kinase C Downregulation in Fibroblasts from Alzheimer's Disease Patients," Neurology, 43:2581-2586 (1993).
Huynh et al., "Reduced Protein Kinase C Immunoreactivity and Altered Protein Phosphorylation in Alzheimer's Disease Fibroblasts," Arch Neurol 46 (1989).
Jin et al., "Changes in Protein Kinases in Brain Aging and Alzheimer's Disease," Drugs &Aging, 6(2):136-149 (1995).
Kanno et al., "The Linoleic Acid Derivative DCP-LA Selectively Activates $PKC_{-E}$, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates $PKC_{-E}$", Dept. of Physiology, Hyogo College of Med., Hyogo, Japan, p. 552 (2006).
Khan et al., "An Internally Controlled Peripheral Biomarker for Alzheimer's Disease: Erk1 and Erk2 responses to the Inflammatory Signal Bradykinin," PNAS, vol. 103, No. 35, pp. 13203-13207, Aug. 29, 2006.
Lee et al., "Ubiquitination of Protein Kinase C-a and Degradation by the Proteasome," J. Biol. Chem., vol. 271, No. 35, pp. 20973-27976, Jun. 3, 1996.
Masliah, "Protein Kinase C Alteration Is an Early Biochemical Marker in Alzheimer's Disease," The Journal of Neuroscience, 11(9): 2759-2767 (1991).
Nagata et al., "FR236924, a Newly Synthesized Derivative of Linoleic Acid, Ameliorates Memory Deficits in Rats Intraventricularly Injected with Amyloid-Beta Peptide." Jpn. J. Physiol. 53,Suppl. 2003(319): S261.
Nagata et al., "The Newly Synthesized Linoleic Acid Derivative CP-LA Ameliorates Memory Deficits in Animal Models Treated with Amyloid-β Peptide and Scopolamine", Psychogeriatrics, 5:22-126 (2003).
NME Digest, Drug News Perspect, 15(10): 666-674 (2002).
Office Action (Restriction Requirement) dated Aug. 10, 2010, in U.S. Appl. No. 11/802,723.
Office Action (Restriction Requirement) dated Jun. 28, 2010, in U.S. Appl. No. 11/698,953.
Office Action dated Jan. 30, 2008, in U.S. Appl. No. 10/933,536.
Office Action dated May 26, 2010, in U.S. Appl. No. 11/802,842.
Office Action dated May 28, 2008, in U.S. Appl. No. 10/933,536.
Office Action dated Feb. 4, 2010, in U.S. Appl. No. 11/802,842.
Office Action dated Jan. 31, 2012, issued in U.S. Appl. No. 12/851,222.
Office Action dated Jul. 20, 2011, in U.S. Appl. No. 11/802,723.
Office Action dated Jul. 7, 2011, in U.S. Appl. No. 11/698,953.
PKC Lab, pp. 1-4, 2010, retrieved from: http://www.pkclab.org/PKC/PKCbiology/PKCbiology_PKC_activators.htm.
Protein Kinase C, pp. 1-6, 2010, retrieved from: http://en.wikipedia.org/wiki/Protein_kinase_C.
Sano et al., "A Controlled Trial of Selegiline, Alpha-Tocopherol, or Both as Treatment for Alzheimer's Disease", New England Journal of Medicine, pp. 1216-1222, Apr. 24, 1997.
Scioletti et al., "Memory Enhancement by Bryostatin in Hermissenda", Biol. Bull., 207:159 (Oct. 2004).
Sun et al., "Dual Effects of Bryostatin-1 on Spatial Memory and Depression", Eur. J. Pharmacol., vol. 512, pp. 43-51, 2005.
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).

Tanzi et al., "The Gene Defects Responsible for Familial Alzheimer's Disease," Neurobiology of Disease, 3:159-168 (1996).
Yaguchi et al., "Effects of cis-unsaturated Free Fatty Acids on $PKC_{-E}$ Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Abramets et al., "Behavioral Depression-Related Modifications of the Properties of Glutamatergic Synapses in the Basolateral Amygdalar Nucleus in Rats," Neurophysiology,34(4):283-293 (2002)
Agranoff et al., "Actinomycin D Blocks Formation of Memory of Shock- Avoidance in Goldfish," Science, 158: 1600-1601 (Dec. 22, 1967).
Bank et al., "Classical Conditioning Induces Long-Term Translocation of Protein Kinase C in Rabbit Hippocampal CA1 Cells", Proc. Natl. Acad. Sci. USA, 85:1988-1992 (Mar. 1988).
Barbas et al., "Multiple Serotonergic Mechanisms Contributing to Sensitization in Aplysia: Evidence of Diverse Serotonin Receptor Subtypes," Serotonin & Memory/Review, 10:373-386 (2003).
Battaini, "Protein Kinase C Isoforms as Therapeutic Targets in Nervous System Disease States," Pharmacological Research, 44(5):353-361 (2001).
Bergold et al., "Protein Synthesis During Acquisition of Long-Term Facilitation is Needed for the Persistent Loss of Regulatory Subunits of the Aplysia cAMP-Dependent Protein Kinase", Proc. Natl. Acad. Sci. USA. 87:3788-3791(May 1990).
Berke et al., "Dopamine and Glutamate Induce Distinct Striatal Splice Forms of Ania-6, an RNA Polymerase II-Associated Cyclin," Neuron, 32:277-287 (Oct. 25, 2001).
Berman et al., "Specific and Differential Activation of Mitogen-Activated Protein Kinase Cascades by Unfamiliar Taste in the Insular Cortex of the Behaving Rat," The Journal of Nueroscience, 18(23);10037-10044 (Dec. 1, 1998).
Besag, "Behavioral Effects of the New Anticonvulsants," Drug Safety, 24(7):513-536 (2001).
Bouron et al. "Acute Application of the Tricyclic Antidepressant Desipramine Presynaptically Stimulates the Exocytosis of Glutamate in the Hippocampus," Neuroscience, 90(3):729-736, (1999).
Budziszewska et al., "Antidepressant Drugs Inhibit Glucocorticoid Receptor-Mediated Gene Transcription—A Possible Mechanism," British Journal of Pharmacology, 130:1385-1393 (2000).
Calo et al., "Pharmacology of Nociceptin and its Receptor: a Novel Therapeutic Target", British Journal of Pharmacology, 129:1261-1283 (2000).
Casini et al., "Carbonic Anhydrase Activators. The Selective Serotonin Reuptake Inhibitors Fluoxetine, Sertraline and Citalopram Are Strong Activators of Isozymes I and II," Bioorganic & Medicinal Chemistry Letters, 13:2765-2768 (2003).
Cavallaro "Memory-Specific Temporal Profiles of Gene Expression in the Hippocampus", PNAS, 99(25):16279-16284 (Dec. 2002).
Cavallaro et al., "Late Memory-Related Genes in the Hippocampus Revealed by RNA Fingerprinting", Proc. Natl. Acad. Sci, USA, 94:9669-9673 (Sep. 1997).
Certified U.S. Appl. No. 60/392,951, filed Jul. 2, 2002.
Chetkovich et al., "N-Methyl-D-Aspartate Receptor Activation Increases cAMP Levels and Voltage-Gated Ca2+ Channel Activity in Area CA1 of Hippocampus", Proc. Natl. Acad. Sci. USA, 88:6467-6471 (Aug. 1991).
Chow, C.K., "Vitamin E Regulation of Mitochondrial Superoxide Generation", Biological Signals and Receptors, 10(1-2): 112-124 ( Jan. 2001).

(56) References Cited

OTHER PUBLICATIONS

Clamp et al., "The Clinical Developments of Bryostatins", Anti-Cancer Drugs, 13(7):673-683 (Aug. 2002).
Cole et al., "Decreased Levels of Protein Kinase C in Alzheimer Brain," Brain Research, 452:165-174 (1988).
Collin et al., "Sequential Modification of membrane currents with classical conditioning" Biophysical J. 54: 955-961 (1988).
Coughlan et al., "Factors influencing the Processing and Function of the Amyloid B Precursor Protein—A Potential Therapeutic Target in Alzheimer's Disease?," Pharmacology & Therapeutics, 86:111-144 (2000).
Coull et al., "Altered Brain Protein Kinase C in Depression: a Post-Mortem Study," European Neuropsychopharmacology, 10:283-288 (2000).
Crow et al., "Inhibition of Protein Synthesis Blocks Long-Term Enhancement of Generator Potentials Produced by One-Trial in Vivo Conditioning in Hermissenda", Proc. Natl. Acad. Sci. USA, 87:4490-4494 (Jun. 1990).
Crow et al., "Protein Synthesis-Dependent and mRNA Synthesis-Independent Intermediate Phase of Memory in Hermissenda," The American Physiological Society, Rapid Communication, 82: 495-500 (1999).
Davis, "The Mitogen-activated Protein Kinase Signal Transduction Pathway," The Journal of Biological Chemistry, 268(20):14553-14556 (Jul. 15, 1993).
Desdouits et al, "Amyloid β Peptide Formation in Cell-free Preparations," The Journal of Biological Chemistry, 271(40):24670-24674 (1996).
Epstein et al., "Time Windows for Effects of Protein Synthesis Inhibitors on Pavlovian Conditioning in Hermissenda: Behavioral Aspects", Neurobiology of Learning and Memory, 79:127-131 (2003).
European Search Report for EP 0574 9738 dated Sep. 10, 2007.
European Search Report for EP 08 01 0738, dated Feb. 2, 2010.
Extended European Search Report issued in EP 12 00 2638 dated Jun. 19, 2012.
Extended European Search Report issued on EP 12005992.8 dated May 24, 2013.
Ezzeddine et al., "Prolonged Habituation of the Gill-Withdrawal Reflex in Aplysia Depends on Protein Synthesis, Protein Phosphatase Activity, and Postsynaptic Glutamate Receptors," The Journal of Neuroscience, 23(29):9585-9594 (Oct. 22, 2003).
Farley et al., "Protein Kinase C Inhibitors Prevent Induction and Continued Expression of Cell Memory in Hermissenda Type B Photoreceptors", Proc. Natl. Acad. Sci. USA, 88:2016-2020 (Mar. 1991).
Ferrari, "Behavioural Pharmacology of Imidazole, a Potential Antidepressant Agent," Arch. Int. Pharmacodyn, 277:303-312 (1985).
Flexner et al., "Effect of Acetoxycycloheximide and of an Acetoxycycloheximide-Puromycin Mixture on Cerebral Protein Synthesis and Memory in Mice," Proc. N.A.S., 55:369-374 (1966).
Gomez et al., "Ca2+ Signaling via the Neuronal Calcium Sensor-1 Regulates Associative Learning and Memory in C. eledans," Neuron, 30:241-248 (Apr. 2001).
Gould et al., "Signaling Networks in the Pathophysiology and Treatment of Mood Disorders," Journal of Psychosomatic Research, 53:687-697 (2002).
Gundlfinger et al., "Different Regulation of Purkinje Cell Dendritic Development in Cerebellar Slice Cultures by Protein Kinase Calpha and -beta," Journal of Neurobiology, 57(1):195-109 (Oct. 2003).
Hahn et al., "Abnormalities in Protein Kinase C Signaling and the Pathphysiology of Bipolar Disorder," Bipolar Disorders, 2:81-86 (1999).
Hayes, "Acetozolamide in Bipolar Affective Disorders," Annals of Clinical Psychiatry, 6(2):91-98 (1994).
Hickman, et al. "Bryostatin 1, a novel antineoplastic agent and protein kinase C activator, induces human myalgia and muscle metabolic defects: A 31P Magnetic Resonance Spectroscopic Study", British Journal of Cancer, 72(4): 998-1003 (1995).

Hu et al., "FGF-18, a Novel Member of the Fibroblast Growth Factor Family, Stimulates Hepatic and Intestinal Proliferation," Molecular and Cellular Biology, 18(10):6063-6074 (Oct. 1998).
Hu et al., "Human Fibroblast Growth Factor-18 Stimulates Fibroblast Cell Proliferation and is Mapped to Chromosome 14p11", Oncogene, 18:2635-2642 (1999).
Hyden et al., "Brain-Cell Protein Synthesis Specifically Related to Learning", Proceedings of the National Academy of Sciences, 65(4);898-904, (Apr. 1970).
Ibarreta et al., "Benzolactam (BL) Enhances sAPP Secretion in Fibroblasts and in PC12 Cells," Neuroreport, 10(5):1035-1040 (1999).
Impey et al., "Making New Connections: Role of ERK/MAP Kinase Signaling in Neuronal Plasticity", Neuron, 23:11-14 (May 1999).
International Preliminary Report on Patentability issued on PCT/US2005/017158, dated Jan. 16, 2007.
International Search Report and Written Opinion for PCT/US2005/028522 dated Apr. 13, 2006.
International Search Report and Written Opinion for PCT/US2006/029110 dated Jan. 2, 2007.
International Search Report and Written Opinion for PCT/US2007/002454 dated Jul. 13, 2007.
International Search Report for PCT/US2003/07101 dated Oct. 17, 2003.
International Search Report for PCT/US2005/017158 dated Dec. 14, 2006.
Ishii et al., "Protein Kinase C Activation and its Role in the Development of Vascular Complications in Diabetes Mellitus," J. Mol. Med., 76:21-31 (1998).
Johnston-Wilson et al., "Disease-specific Alterations in Frontal Cortex Brain Proteins in Schizophrenia, Bipolar Disorder, and Major Depressive Disorder," Molecular Psychiatry, 5:142-149 (2000).
Katzoff et al., "Nitric Oxide Is Necessary for Multiple Memory Processes after Learning That a Food Is Inedible in Aplysia," The Journal of Neurosciences, 22(21):9581-9594 (Nov. 1, 2002).
Kornhauser et al., "A Kinase to Remember: Dual Roles for MAP Kinase in Long-Term Memory", Neuron, 18:839-842 (Jun. 1997).
Kosik et al., "Microtubule-associated Protein 2: Monoclonal Antibodies Demonstrate the Selective Incorporation of Certain Epitopes into Alzheimer Neurofibrillary Tangles", Proc. Natl. Acad. Sci. USA, 81:7941-7945 (Dec. 1984).
Kunisaki et al., "Normalization of diacylglycerol-protein kinase C activation by vitamin E in aorta of diabetic rats and cultured rat smoth muscle cells exposed to elevated glucose levels." Diabetes, 43: 1372-1377 (1994).
Kuzirian et al., "Bryostatin and lactacystin affect PKC activation and long-term memory," Database Biosis [Online], Biosciences Information Service, Mar. 2006, Abstract.
Kuzirian et al., "Bryostatin Enhancement of Memory in Hermissenda", Biol. Bull. 210:201-214 (Jun. 2006).
Kuzirian et al., "Paviovian Conditioning-Specific Increases of the Ca2+and GTP-Binding Protein, Calexcitin in Identified Hermissenda Visual Cells", Journal of Neurocytology, 30:993-1008 (2001).
Lamberti et al., "Antideppressant-like effects of endogenous histamine and of two histamine H1 receptor agonists in the mouse forced swim test", British Journal of Pharmacology, 123(7): 1331-1336 (Jan. 1, 1998).
Lenox et al., "Lithium and the Brain: A Psychopharmacological Strategy to a Molecular Basis for Manic Depressive Illness," Clin. Chem, 40(2):309-314 (1994).
Leontieva et al., "Identification of Two Distinct Pathways of Protein Kinase Ca Down-regulation in Intestinal Epthelial Cells", The Journal of Biological Chemistry, 279(7):5788-5801 (2004).
Li et al., "Endothelin Receptor Antagonist CPU0213 and Vitamin E Reverse Downregulation of FKBP12.6 and SERCA2a: A Role of Hyperphosphorylation of $PKC_E$," European Journal of Pharmacology, 591:211-18 (2008).
Lieb et al., "Valproic Acid inhibits substance P-induced Activiation of Protein Kinase C Epsilon and Expression of the Substance P Receptor," Journal of Neurochemistry, 86:69-76 (2003).

(56) References Cited

OTHER PUBLICATIONS

Lu et al., "Activiation of Protein Kinase C Triggers Its Ubiquitination and Degradation," Molecular and Cellular Biology, 18(2): 839-845 (Feb. 1998).
Lyketsos, "Treating Depression in Alzheimer Disease, Efficacy and Safety of Sertraline Therapy, and the Benefits of Depression Reduction: The DIADS", Arch Gen Psychiatry, 60: 737-746 (2003).
Manji et al. "Protein Kinase C Signaling in the Brain: Molecular Transduction of Mood Stabilization in the Treatment of Manic-Depressive Illness," Biol. Psychiatry 46(10):1328-1351 (1999).
Manji et al., "Post-receptor Signaling Pathways in the Pathophysiology and Treatment of Mood Disorders," Current Psychiatry Reports, 20(6): 476-489 (2000).
Mannisto et al., "Beneficial Effects of Co-administration of Catechol-O-Methyltransferase Inhibitors and L-dihydroxyphenylalanine in Rat Models of Depression", European Journal of Pharmacology, 274:229-233 (1995).
Martin et al., "Role of vitamin E and C on neurodegenerative diseases and cognitive performance," Nutrition Review, 60(11): 308-326 (2002).
Masson et al., "Neurotransmitter Transporters in the Central Nervous System," Pharmacological Reviews,51(3):439-464 (1999).
Matsui et al., "The Role of Growth Factors in the Activity of Pharmacological Differentiation Agents," Cell Growth and Differentiation, 13(6) (Jun. 2002), pp. 275-283.
McPhie et al., "Cell Specificity of Molecular Changes During Memory Storage", Journal of Neurochemistry, 60(2):646-651 (1993).
Mody et al., "Genome-wide gene expression profiles of the developing mouse hippocampus,", PNAS, 98(15):8862-8867 (Jul. 17, 2001).
Morishita et al., "Different Effect of Desipramine on Protein Kinase C in Platelets Between Bipolar and Major Depressive Disorders," Psychiatry and Clinical Neurosciences, 53:11-15 (1999).
Morshita et al., "Effects of Tricylic Antidepressants on Protein Kinase C Activity in Rabbit and Human Platelets in Vivo," Journal of Affective Disorders, 70:329-332 (2002).
Muscat et al., "Antidepressant-Like Effects of Dopamine Agonists in an Animal Model of Depression," Biol Psychiatry, 31: 937-946 (1992).
Mutter et al., "Chemistry and Clinical Biology of the Byostatins," Bioorganic & Medicinal Chemistry, 8:184-1860 (2000).
Nelson et al., "Isolation of a G Protein That Is Modified by Learning and Reduces Potassium Currents in Hermissenda," Science, 247:1479-1483 (Mar. 23, 1990).
Nelson et al., "Specific High Molecular Weight mRNAs Induced by Associative Learning in Hermissenda", Proc. Nat. Acad. Sci. USA, 87:269-273 (Jan. 1990).
Office Action (Final) dated Dec. 3, 2013, in U.S. Appl. No. 12/883,444.
Office Action dated Feb. 19, 2014, in U.S. Appl. No. 13/042,892.
Office Action dated Jun. 26, 2013, in U.S. Appl. No. 12/833,444.
Office Action dated Sep. 18, 2012, in U.S. Appl. No. 13/042,892.
Office Action dated Sep. 5, 2012, in U.S. Appl. No. 12/538,245.
Office Action (Final) dated Dec. 2, 2013, in U.S. Appl. No. 11/802,842.
Office Action (Restriction Requirement) dated Mar. 7, 2011, in U.S. Appl. No. 10/594,420.
Office Action dated Aug. 15, 2011, in U.S. Appl. No. 10/594,420.
Office Action dated Jan. 24, 2014, in U.S. Appl. No. 13/851,161.
Office Action dated Jul. 16, 2013, in U.S. Appl. No. 11/802,842.
Office Action dated May 22, 2013, in U.S. Appl. No. 13/561,770.
Office Action dated May 4, 2012, in U.S. Appl. No. 13/152,616.
Office Action dated Nov. 4, 2013, in U.S. Appl. No. 12/538,245.
Ohbayashi et al., "Structure and Expression of the mRNA Encoding a Novel Fibroblast Growth Factor, FGF-18," The Journal of Biological Chemistry, 273(29):18161-18164 (1998).
Olds et al., "Discrimination Learning Alters the Distribution of Protein Kinase C in the Hippocampus of Rats," The Journal of Neurosciences, 10(11):3707-3713 (Nov. 1990).
Olds et al., "Imaging of Memory-Specific Changes in the Distribution of Protein Kinase C in the Hippocampus", Science, 245:866-869 (Aug. 25, 1989).
Ortega et al., "Cognitive Function in Elderly People is Influenced by Vitamin E status." J. Nutrition, 132(7):2065-2068 (2002).
Pandey et al., "Protein Kinase C in Platelets of Depressed Patients," Biological Psychiatry, 44:909-911 (1998).
Pandey et al., "Protein Kinase C and Phospholipase C Activity and Expression of Their Specific Isozymes is Decreased and Expression of MARCKS is Increased in Platelets of Bipolar but Not in Unipolar Patients," Neuropschoparmacology, 26(2):216-228 (2002).
Partial European Search Report EP 08 01 0738, dated Oct. 6, 2009.
Partial European Search Report EP 12005992.8, dated Jan. 31, 2013, 8 pages.
Pettit et al., "Antineoplastic Agents 224 Isolation and Structure of Neristatin 1," Journal of the American Chemical Society, 113(17):6693-6695 (1991).
Popoli et al., "Second Messenger-Regulated Protein Kinases in the Brain: Their Functional Role and the Action of Antidepressant Drugs," J. Neurochem.74(1):21-31 (2000).
Prevostel et al., "Protein Kinase Ca Actively Downregulates Through Caveolae-Dependent Traffic to an Endosomal Compartment," Journal of Cell Science, 113:2575-2584 (2000).
Quattrone et al., "Posttranscriptional Regulation of Gene Expression in Learning by the Neuronal ELAV-Like mRNA-Stabilizing Proteins", PNAS, 98( 20): 11668-11673 (Sep. 25, 2001).
Rampello et al., "Dopamine and Depression: Therapeutic Implications" CNS Drugs, 13(1): 35-42 (Jan. 1, 2000).
Ricarelli et al., Vitamin E: Protective Role of a Janus Molecule. The FASEB Journal, 15:2314-2315 (2005).
Schrenk et al., "Altered Dendritic Development of Cerebellar Purkinje Cells in Slice Cultures from Protein Kinase Cgamma-deficient Mice," Neuroscience 110(4):675-689 (2002).
Shelton, "Cellular Mechanisms in the Vulnerability to Depression and Response to Antidepressants," Depression, 23(4) : 713-729 (Dec. 2000).
Smith et al., "Inhibition of the proteasome converts bryostatin from an antagonist to an agonist of protein kinase C (PKC)," FASEB Journal, Fed. of American Soc. For Experimental Biology, US, 11(9): A987 (Jan. 1, 1997).
Sun et al., "Carbonic Anhydrase Gating of Attention: Memory Therapy and Enhancement," TRENDS in Pharmacological Sciences, 23(2): 83-89 (Feb. 2002).
Sun et al., "Depressed or Demented: Common CNS Drug Targets?!", Current Drug Targets—CNS & Neurological Disorders, 1: 575-592 (2002).
Sun et al., "Functional Switching of GABAergic Synapses by Ryanodine Receptor Activation," Proc. Nat'l. Acad. Sci USA, 97(22):12300-12305 (2000).
Sun et al., "Synergistic Effects of Chronic Bryostatin-1 and Alpha-tocopherol on Spatial Learning and Memory," Eur. J. Pharmacol., 584:328-337 (2008).
Supplemental Partial European Search Report for EP03742389 dated Aug. 17, 2007.
Supplementary European Search Report for PCT/US2003/07101 dated Jun. 6, 2008.
Supuran et al., Carbonic Anhydrase Activators. XV. A Kinetic Study of Interaction of Bovine Isozyme II with Pyrazoles, Bis- and Tris-azolyl-methanes:, Biol. Pharm. Bull., 19(11):1417-1422 (1996).
Suzuki et al., "Altered 5-HT-Induced Calcium Responge in the Presence of Staurosporine in Blood Platelets from Bipolar Disorder Patients," Neuropsychopharmacology, 28:1210-1214 (2003).
Talk et al., "Neurophysiological Substrates of Context Conditioning in Hermissenda Suggest a Temporally Invariant Form of Activity-Dependent Neuronal Facilitation", Neurobiology of Learning and Memory, 72:95-117 (1999).
Tischmeyer et al., "Activation of Immediate Early Genes and Memory Formation", CMLS, Cell. Mol. Life Sci., 55:564-574 (1999).
Tsien et al., "The Essential Role of Hippocampal CA1 NMDA Receptor-Dependent Synaptic Plasticity in Spatial Memory," Cell, 87:1327-1338 (Dec. 27, 1996).

(56) References Cited

OTHER PUBLICATIONS

U.S. Department of Health and Human Services Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 6, 2005, Pharmacology and Toxicology, 30 pages.
Vrontakis et al., "Current Drug Targets-CNS & Neurological Disorders. Glanain: A Biologically Active Peptide," Abstract 1(6):531-541 (2002).
Wang et al., "Flouxetine Depresses Glutamate Exocytosis in the Rat Cerebrocortical Nerve Terminals (Synaptosomes) via Inhibition of p/a Ca2+ Channels," Synapse, 48:170-177 (2003).
Wang et al., "Increased Membrane-Associated Protein Kinase C Activity and Translocation in Blood Platelets from Bipolar Affective Disorder Patients," Journal of Psychiatric Research, 33:171•179 (1999).
Wender, "Role of the A-Ring of Bryostatin Analogues in PKkC Binding: Synthesis and Initial Biological Evaluation of New A-Ring Modified," Bryologs. Organic Letters, 7(10):1995-1998 (2005).
Wilkinson et al., "Research Communication: Isoenzyme specificity of bisindolylmaleimides, selective inhibitors of protein kinase C", Biochem. J. (1993) 294, 335-337.
Woolf et al., "Hippocampal Microtubule-associated Protein-2 Alterations with Contextual Memory", Brain Research, 821(1):241-249 (Mar. 6, 1999).
Yamanouchi et al., "Early Forms of Microtubule-associated Protein are Strongly Expressed in Cortical Dysplasia", Acta Neuropethol, 95:466-470 (1998).
Yildiz, "Phosphoinositide metabolism, lithium and manic depresive illness," Spectroscopy 16:307-316 (2002).
Zhang et al., "Citron Binds to PSD-95 at Glutamatergic Synapses on Inhibitory Neurons in the Hippocampus," The Journal of Neuroscience, 19(1):96-108 (Jan. 1, 1999).
Zhang et al., "Preclinical Pharmacology of the Natural Product Anticancer Agent Bryostatin 1, an Activator of Protein Kinase C1." Cancer Research, 56:802-808 (1996).
Zhao et al., "Spatial learning induced changes in expression of the ryanodine type II receptor in the rat hippooampus," The FASEB Journal, 14: 290-300, Feb. 2000.
Zhen et al., "The p38 Mitogen-Activated Protein Kinase is Involved in Associative Learning in Rabbits," The Journal of Neuroscience, 2(15):5513-5519 (Aug. 1, 2001).
Alkon et al., "Reduction of two voltage-dependent K+ currents mediates retention of a learned association", Behav. Neural Biol., vol. 44, pp. 278-300, 1985.
Alkon et al., "Regulation of Hermissenda K+ Channels by Cytoplasmic and Membrane-Associated C-Kinase," J. Neurochem., 51(3):903-916 (1988).
Ashendel et al., "Protein Kinase Activity Associated With a Phorbol Ester Receptor Purified from Mouse Brain", Cancer Res., vol. 43, pp. 4333-4337, 1983.
Baltuch, G.H. et al., "Protein Kinase C Inhibitors Suppress Cell Growth in Established and Low-passage Glioma Cell Lines. A Comparison Between Staurosporine and Tamoxifen", Neurosurgery, Sep. 1993, vol. 33, No. 3, pp. 495-501.
Bennett et al., "Expression Analysis of BACE2 in Brain and Peripheral Tissues," The Journal of Biological Chemistry, 275(27):29647-20651 (2000).
Bergamaschi et al., "Defective Phorbol Ester-Stimulated Secretion of B-Amyloid Precursor Protein from Alzheimer's Disease Fibroblasts," Neuroscience Letters, 201:1-4 (1995).
Bhagavan et al., "Restoration of TEA-Induced Calcium Responses in Fibroblasts from Alzheimer's Disease Patients by a PCK Activator," Neurobiol. Disease, 5:177-187 (1998).
Birkmayer, "L-Deprenyl Plus L. Phenylalanine in the Treatment of Depresssion," Journal of Neural Transmission, 59:81-87 (1984).
Blobe et al.,"Regulation of protein kinase C and role in cancer biology,"Cancer Metast. Rev. 1994; 13:411-431.

Burry, R. W., "PKC Activators (Phorbol Ester or Bryostatin) Stimulate Outgrowh of NGF-Dependent Neurites in a Subline of PC12 Cells," Journal of Neurosciences Research, 53:214-222 (1998).
Bursell S.E. et al., "Can Protein Kinase C Inhibition and Vitamin E Prevent the Development of Diabetic Vascular Complications?",Diabetes Research and Clinical Practice, vol. 45, No. 2/03, Jan. 1999, pp. 169-182.
Cai et al., "BACE1 is the major β-secretase for Generation of AβPeptides by Neurons," Nature Neuroscience, 4(3):233-234 (Mar. 2001).
Calingasan et al., "Accumulation of Amyloid Precursor Protein-like Immunoreactivity in Rat Brain in Response to Thiamine Deficiency", Brain Research, Apr. 17, 1995, vol. 677, No. 1, p. 50.
Caputi et al., "Increased Secretion of the Amino-Terminal Fragment of Amyloid Precursor Protein in Brains of Rats with a Constitutive Up-Regulation of Protein Kinase C," J. Neurochem., 68(6):2523-2529 (1997).
De Lorenzo et al., "Bryostatin-1 Stimulates the Transcription of Cyclooxygenase-2: Evidence for an Activator Protein-1-Dependent Mechanism", Clinical Cancer Research, 9:5036-5043 (2003).
Efthimiopoulos et al., "Intracellular Cyclic AMP Inhibits Constitutive and Phorbol Ester-Stimulated Secretory Cleavage of Amyloid Precursor Protein," J. Neurochem., 67(2):872-875 (1996).
Eriksen, "Linking Work Factors toNeck Myalgia:The Nitric Oxide/ Oxygen Ratio Hypothesis", Medical Hypotheses 62:721-726 (2004).
Esler et al., "A Portrait of Alzheimer Secretases—New Features and Familiar Faces," Science, 293:1449-1454 (2001).
Etcheberrigaray et al., "Classical conditioning and protein kinase C activation regulate the same single potassium channel in Hermissenda crassicornis photoreceptors", Proc Natl Acad Sci USA, 89: 7184-8, 1992.
Extended European Search Report in 14001452.3 dated Jun. 30, 2014.
Extended European Search Report, for EP Application No. 14001303.8 dated Nov. 21, 2014.
Gabuzda et al., "Inhibition of β-Amyloid Production by Activation of Protein Kinase C,"J. Neurochem., 61(6):2326-2329 (1993).
Ghosh et al., "Design of Potent Inhibitors for Human Brain Memapsin 2 (β.-Secretase)," J. Am. Chem. Soc., 122(14):3522-3523 (2000).
Glazer, R.I., "Protein Kinase C in Multidrug Resistance, Neoplastic Transformation, and Differentiation", Protein Kinase C, New York Oxford Oxford University Press, pp. 171-198, (1994).
Goekjian, et al., "Protein Kinase C in the Treatment of Disease: Signal Transduction Pathways, Inhibitors, and Agents in Development," Current Medicinal Chemistry, 6:877-903 (1999).
Govoni et al., "Fibroblasts of Patients Affected by Down's Syndrome Oversecrete Amyloid Precursor Protein and are Hyporesponsive to Protein Kinase C Stimulation," Neurology, 46:1069-1075 (1996).
Hanui et al., "Characterization of Alzheimer's β-Secretase Protein BACE," The Journal of Biological Chemistry, 275(28):21099-21106 (2000).
Hardy, "Amyloid, the Presinilins and Alzheimer's Disease," TINS, 20(4): 154-159 (1997).
Hardy, "Molecular Genetics of Alzheimer's Disease," Acta Neurol Scand, Supplemental, 165:13-17 (1996).
Hennings et al., "Bryostatin 1, an activator of protein kinase C, inhibits tumor promotion by phorbol esters in SENCAR mouse skin," (1987) Carcinogenesis 8(9): 1343-46.
Hickman et al., "Bryostatin 1, A Novel Antineoplastic Agent and Protein Kinase C Activator, Induces Human Myalgia and Muscle Metabolic Defects: A P Magnetic Resonance Spectroscopic Study", British Journal of Cancer, 72:998-1003 (1975).
Hoelting et al., "12-0-tetradecanoyl-phorbol-13-acetate (TPA) Counteracts the Anti-Proliferative and Antiinvasive Effects of Tamoxifen in a Metastatic Follicular Thyroid Cancer Cell Line", Proc. Am. Cancer Res., Mar. 1995, vol. 36, Abstract No. 481.
Hofmann, "The Potential for Isoenzyme-Selective Modulation of Protein Kinase C," The FASEB Journal, 11:649-669 (1997).

(56) References Cited

OTHER PUBLICATIONS

House et al., "Protein kinase C contains a pseudosubstrate prototope in its regulatory domain." Science, vol. 238, No. 4834, pp. 1726-1728, Dec. 1987.
Howe, C. et al., "Differetial Effect of the Manipulation of Protein Kinase C Activity on Normal Versus Leukemic Progenitor Cell Response to rGM-CSF", Proc. Am. Assoc. Cancer Res., Mar. 1989, vol. 30, Abstract No. 244.
Hug et al., "Protein kinase C isoenzymes: divergence in signal transduction?" Biochem J. 1993;291:329.
Hung et al., "Activation of Protein Kinase C Inhibits Cellular Production of the Amyloid β-Protein," The Journal of Biological Chemistry, 268(31):22959-22962 (1993).
Jayson et al.., "A phase I trial of bryostatin 1 in patients with advanced malignancy using a 24 hour infusion." British Journal of Cancer, vol. 72, pp. 461-468, 1995.
Jolly-Tornetta et al., "Protein Kinase C Regulation of Intracellular and Cell Surface Amyloid Precursor Protein (APP) Cleavage in CH0695 Cells," Biochemistry, 39:15282-15290 (2000).
Jolly-Tornetta et al., "Regulation of Amyloid Precursor Protein (APP) Secretion by Protein Kinase Cα in Human Ntera 2 Neurons (NT2N)," Biochemistry, 39(25):7428-7435 (2000).
Katzman, "Alzheimer's disease," New England Journal of Medicine, 1986;314:964-973.
Kikkawa et al., "Calcium-activated, phospholipid-dependent protein kinase from rat brain. Subcellular distribution, purification, and properties." J. Biol. Chem. vol. 257, pp. 13341-13348, 1982.
Kikkawa et al., "The Protein Kinase C Family: Heterogeneity and its Implications," Ann. Rev. Biochem, vol. 58, pp. 31-44, 1989.
Kim et al, "Amyloid Precursor Protein Processing is Separately Regulated by Protein Kinase C and Tyrosine Kinase in Human Astrocytes," Neurosci. Letters, 324(3):184-188 (May 2002).
Kinouchi et al., "Conventional Protein Kinase C (PKC)-α and Novel PKCE, But Not -δ, Increase the Secretion of an N-Terminal Fragment of Alzheimer's Disease Amyloid Precursor Protein from PKC cDNA Transfected 3Y1 Fibroblasts," FEBS Letters, 364:203-206 (1995).
Kogure, K. et al., "Alpha-Tocopheryl Succinate Activates Protein Kinase C in Cellular and Cell-free Systems", Journal of Nutritional Science and Vitaminology, Oct. 2003, vol. 49, No. 5, pp. 310-314.
Kozikowski et al., "Modeling, Chemistry, and Biology of the Benzolactam Analogues of Indolactam V (ILV). 2. Identification of the Binding Site of the Benzolactams in the CRD2 Activator-Binding Domain in PKCs and Discovery of an ILV Analogue of Improved Isozyme Selectivity," J. Med. Chem.,40:1316-1326 (1997).
Kravitz et al., "Dietary Supplements of Phenylalanine and Other Amino Acid Precursors of Brain Neuroamines in the Treatment of Depressive Disorders", Journal of the American Osteopathic Associate, 84(1 Suppl):119-123 (Sep. 1984).
Kuzirian et al., Database Medline (Online), Abstract, "Bryostatin Enhancement of Memory in Hermissenda," Jun. 2006 Database Accession No. NLM 16801495.
Maiorini et al., "Potential Novel Targets for Alzheimer Pharmacotherapy: I. Secretase," Journal of Clinical Pharmacy and Therapeutics, 27:169-183 (2002).
Marshall et al., "Phase 1 Study of Prolonged Infusion Bryostatin-1 in Patients with Advanced Malignancies", Cancer Biology & Therapy 1:4, 409-416 (Jul./Aug. 2002).
Masliah et al., "Role of Amyloid Precursor Protein in the Mechanisms of Neurodegeneration in Alzheimer's Disease," Laboratory Investigation, 77(3):197-209 (1997).
McKhann et al., "Clinical diagnosis of Alzheimer's disease: report of the NINCDS-ADRDA Work Group under the auspices of Department of Health and Human Services Task Force on Alzheimer's Disease", Neurology, vol. 34. No. 7, pp. 939-944, Jul. 1984.
McLoughlin et al., "Muscle Pains and Biochemical Changes Following Suxamethonium Administration After Six Pretreatment Regimens", Anaesthesia, 47:202-206 (1992).

Namba, Y. et al., "Apolipoprotein E Immunoreactivity in Cerebral Amyloid Deposits and Neurofibrillary Tangles in Alkzheimer's Disease and Kuru Plaque Amyloid in Creutzfeldt-Jakob Disease", Brain Research, Feb. 8, 1991, vol. 541, No. 1, pp. 163-166.
Nan et al., "Dual Function Glutamate-Related Ligands: Discovery of a Novel, Potent Inhibitor of Glutamate Carboxypeptidase II Possessing mGluR3 Agonist Activity," Journal of Medicinal Chemistry, 43(5):772-774 (2000).
Nishizuka, Y., "Studies and prospectives of the protein kinase C family for cellular regulation", Cancer, vol. 63, pp. 1892-1903, 1989.
Office Action dated Nov. 17, 2014, in U.S. Appl. No. 12/883,444.
Office Action (final) dated Jun. 11, 2014 in U.S. Appl. No. 12/538,245.
Office Action (Final) dated Jun. 26, 2014 in U.S. Appl. No. 13/042,892.
Office Action (non-final) dated Nov. 4, 2014, in co-pending U.S. Appl. No. 11/802,842.
Patella et al., "The Antineoplastic Bryostatins Affect Human Basophils and Mast Cells Differently," Blood, 85(5):1272-1281 (1995).
Prendville et al., "A phase I study of intravenous bryostatin 1 in patients with advanced cancer", British J Cancer., vol. 68. No. 2, pp. 418-424, 1993.
Price, D.L. et al., "Alzheimer Disease and the Prion Disorders Amyloid .beta.-protein and Prion Protein Amyloidoses", Proceedings of the National Academy of Sciences of USA, Jul. 15, 1993, vol. 90, No. 14, pp. 6381-6384.
Robner et al., "Short Communication: Protein Kinase Cα and β1 Isoforms are Regulators of α-Secretary Proteolytic Processing of Amyloid Precursor Protein in Vivo," European Journal of Neuroscience, 13:1644-1648 (2001).
Sanchez-Andres et al., "Voltage-clamp analysis of the effect of classical conditioning on the hippocampus", J Neurophysiol. 65: 796-807, 1991.
Savage et al., "Turnover of Amyloid β-Protein in Mouse Brain and Acute Reduction of Its Level by Phorbol Ester," The Journal of Neuroscience, 18(5):1743-1752 (1998).
Scheuner et al., "Secreted Amyloid β-Protein Similar to that in the Senile Plaques of Alzheimer's Disease is Increased in Vivo by the Presenilin 1 and 2 and App Mutations linked to Familial Alzheimer's Disease," Nature Medicine, 2(8) (1996).
Selkoe, "Alzheimer's Disease: Genes, Proteins, and Therapy," Physiological Reviews, 81(2):741-766 (2001).
Selkoe, "Normal and Abnormal Biology of the β-Amyloid Precursor Protein," Annu. Re. Neurosci., 17:489-517 (1994).
Selkoe, "Translating Cell Biology into Therapeutic Advances in Alzheimer's Disease," Nature, 399(24):A23-A31 (1999).
Shimohama et al., "Assessment of Protein Kinase C Isozymes by Two-Site Enzyme Immunoassay in Human Brains and Changes in Alzheimer's Disease," Neurology, 43:1407-1413 (1993).
Shoulson, "Experimental Therapeutics of Odenegerative Disorders: Unmet Needs," Science, 282:1072-1074 (1998).
Sinha et al., "Purification and Cloning of Amyloid Precursor Protein β-Secretase from Human Brain," Nature, 402:537-540, (1999).
Skovronsky et al., Protein Kinase C-Dependent α-Secretase Competes with β-Secretase for Cleavage of Amyloid-β Precursor Protein in the Trans-Golgi Network, The Journal of Biological Chemistry, 275(4):2568-2575 (2000).
Small et al., "Alzheimer's Disease and the Amyloid β. Protein: What is the Role of Amyloid?," Journal of Neurochemistry, 73(2):443-449 (1999).
St. George-Hyslop et al., "The genetic defect causing familial Alzheimer's disease maps on chromosome 21", Science, vol. 235, No. 4791, pp. 885-890, Feb. 1987.
Szallasi et al., "Differential Regulation of Protein Kinase C Isozymes by Cryostatin 1 and Phorbol 12-Myristate 13-Acetate in NIH 3T3 Fibroblasts," Journal of Biological Chemistry, 269(3):2118-2124 (1994).
Tanzi et al., "Protease Inhibitor domain encoded by an amyloid protein precursor mRNA associated with Alzheimer's disease," Nature, 1988; 331:528-530.

(56) References Cited

OTHER PUBLICATIONS

Turner et al., "Specificity of Memapsin 1 and Its Implications on the Design of Memapsin 2 (β-Secretase) Inhibitor Selectivity," Biochemistry, 41:8742-8746 (2002).
Varterasian et al., "Phase II Trial of Bryostatin 1 in Patients with Relapsed Low-Grade Non-Hodgkin's Lymphoma and Chronic Lymphocytic Leukemia," Clinical Cancer Research, vol. 6, pp. 825-828, 2000.
Vassar et al., A-Generating Enzymes: Recent Advances in Band y-Secretase Research, Neuron, 27:419-422 (2000).
Vassar et al., "Secretase Cleavage of Alzheimer's Amyloid Precursor Protein by the Transmembrane Aspartic Protease BACE," Science, 286:735-741 (1999).
Wang et al., "Attenuated Protein Kinase C Activity and Translocation in Alzheimer's Disease Brain," Neurobiology of Aging, 15(3):293-298 (1994).
Webb et al., "Protein Kinase C Isoenzymes: A Review of Their Structure, Regulation and Role in Regulating Airways Smooth Muscle Tone and Mitogenesis," British Journal of Pharmacology, vol. 30, pp. 1433-1452, 2000.
Weitman et al., "A Phase I Trial of Bryostatin-1 in Children with Refractory Solid Tumors: A Pediatric Oncology Group Study", Clinical Cancer Research, vol. 5, pp. 2344-2348, 1999.
Wiltfang et al., "Molecular Biology of Alzheimer's Dementia and Its Clinical Relevance to Early Diagnosis and New Therapeutic Strategies," Gerontology, 47:65-71 (2001).
Xu et al., "Metabolish of Alzheimer β-Amyloid Precursor Protein; Regulation by Protein Kinase A in Intact Cells and in a Cell-Free System," Proc. Natl. Acad. Sci. USA, 93:4081-4084 (1996).
Yaguchi et al., "The CIS-Unsaturated Free Fatty Acid Derivative Hepba Regulates a7 Nicotinic ACh receptor Trafficing", Dept. αf Physiology, Hyogo College of Med., Hyogo, Japan, Bulletin of the Japanese Society for Neurochemistry, 2008, 47(2/3): 222.
Yamada, K. et al., "Protective Effects of Idebenone and Alpha-tocopherol on Beta-amyloid-(1-42)-induced Learning and Memory Deficits in rats: Implication of Oxidative Stress in Beta-amyloid-induced Neurotoxicity in vivo", Jan. 1999, vol. 11, No. 1, pp. 83-90.
Cochinov, "Depression in cancer patients", Lancet Oncology, 2:499-505 (2001).
Extended European Search Report in 15002036.0 dated Nov. 2, 2015.
Office Action (Final) dated Jun. 9, 2015, in U.S. Appl. No. 11/802,842.
Office Action (final) dated Jan. 20, 2016 in U.S. Appl. No. 13/669,353.
Office Action (final) dated Jul. 13, 2015, in co-pending U.S. Appl. No. 12/883,444.
Office Action (non-final) dated Apr. 7, 2015, in U.S. Appl. No. 13/669,353.
Office Action dated Feb. 1, 2016, U.S. Appl. No. 11/802,842.
Office Action dated Feb. 13, 2015, in U.S. Appl. No. 13/660,567.
Office Action dated Feb. 4, 2016, U.S. Appl. No. 13/851,161.
Office Action dated Sep. 21, 2015, in U.S. Appl. No. 13/042,892.
Lee et al., "Dephosphorylation of activated protein kinase C contributes to downregulation by bryostatin," Am. Physiological Soc. 1996, C304-C311.
Office Action (final) dated May 5, 2016, U.S. Appl. No. 13/042,892.
Office Action dated Jun. 1, 2016, in U.S. Appl. No. 14/196,455.
Office Action dated Jan. 12, 2017, in U.S. Appl. No. 13/669,353.
Office Action dated Nov. 30, 2016, U.S. Appl. No. 13/042,892.
Office Action (Final) dated Aug. 31, 2016, in U.S. Appl. No. 11/802,842.
Office Action dated Mar. 20, 2017, in U.S. Appl. No. 11/802,842.

* cited by examiner

THERAPEUTIC EFFECTS OF BRYOSTATINS, BRYOLOGS, AND OTHER RELATED SUBSTANCES ON HEAD TRAUMA-INDUCED MEMORY IMPAIRMENT AND BRAIN INJURY

This application claims benefit to U.S. Provisional Application Ser. No. 60/900,338 filed on Feb 9, 2007 and to U.S. Provisional Application Ser. No. 60/924,663, filed on May 24, 2007, all of which are hereby incorporated herein by reference in their entireties.

FIELD OF THE INVENTION

The present invention relates to the treatment of head trauma with compounds that activate protein kinase C (PKC) or boost nerve growth factor (NGF), brain-derived neurotrophic factor (BDNF) or other neurotrophic factors.

BACKGROUND OF THE INVENTION

A. Head Trauma

Head injury is a trauma to the head, that may or may not include injury to the brain (see also brain injury). The incidence (number of new cases) of head injury is 300 per 100,000 per year (0.3% of the population), with a mortality of 25 per 100,000 in North America and 9 per 100,000 in Britain. Head trauma is a common cause of childhood hospitalization.

Head injuries include both injuries to the brain and those to other parts of the head, such as the scalp and skull. Head injuries may be closed or open. A closed (non-missile) head injury is one in which the skull is not broken. A penetrating head injury occurs when an object pierces the skull and breaches the dura mater. Brain injuries may be diffuse, occurring over a wide area, or focal, located in a small, specific area. A head injury may cause a skull fracture, which may or may not be associated with injury to the brain. Some patients may have linear or depressed skull fractures. If intracranial hemorrhage, or bleeding within the brain occurs, a hematoma within the skull can put pressure on the brain. Types of intracranial hematoma include subdural, subarachnoid, extradural, and intraparenchymal hematoma. Craniotomy surgeries are used in these cases to lessen the pressure by draining off blood. Head trauma is caused by a concussive event.

Brain injury can be at the site of impact, but can also be at the opposite side of the skull due to a contrecoup effect (the impact to the head can cause the brain to move within the skull, causing the brain to impact the interior of the skull opposite the head-impact). If the impact causes the head to move, the injury may be worsened, because the brain may ricochet inside the skull (causing additional impacts), or the brain may stay relatively still (due to inertia) but be hit by the moving skull.

B. Protein Kinase C

PKC has been identified as one of the largest gene families of non-receptor serine-threonine protein kinases. Since the discovery of PKC in the early eighties by Nishizuka and coworkers (Kikkawa et al. (1982) *J. Biol. Chem.* 257: 13341), and its identification as a major receptor for phorbol esters (Ashendel et al. (1983) *Cancer Res.*, 43: 4333), a multitude of physiological signaling mechanisms have been ascribed to this enzyme. The intense interest in PKC stems from its unique ability to be activated in vitro by calcium and diacylglycerol (and its phorbol ester mimetics), an effector whose formation is coupled to phospholipid turnover by the action of growth and differentiation factors.

The activation of PKC has been shown to improve learning and memory. (U.S. patent application Ser. Nos. PCT/US02/13784; PCT/US03/07102; 60/287,721; 60/362,081; 10/172,005; and 10/476,459; each incorporated herein by reference in its entirety). Prior to the present disclosure, however, the PKC-mediated improvement of learning and memory has not been recognized as a mechanism for the treatment of post-head trauma memory deficits and brain injury. Also, the PKC activators disclosed herein, specifically those compounds that improve learning and memory, were not recognized as possessing brain function-restoring activity after head trauma.

Head trauma therapy has historically been limited to few treatment options available. Although many types of potential neuroprotectants have been tested in clinical trials, none has been approved for clinical use, because of ineffectiveness especially when used post-head trauma or associated toxicity. The compounds presented in this invention disclosure were effective when the treatment was started one hour after the head trauma in the animal model at doses that have already been demonstrated to be well tolerated in humans (the bryostatin-1 doses). Compounds that target the protein kinase C(PKC) such as bryostatin-1, a direct PKC activator, and methylcatechol diacetic acid, a derivative of methylcatechol, an enhancer of nerve growth factor (NGF), brain-derived neurotrophic factor (BDNF) or other neurotrophic factors, which is perhaps one of the PKC targets, have been found to have therapeutic value against brain injury and memory impairment induced with head trauma. The development of these substances as therapeutic in the treatment of head trauma is provided by this invention.

SUMMARY OF THE INVENTION

The present invention provides methods of treating head trauma comprising the steps of identifying a subject having suffered a head trauma and administering to said subject an amount of a pharmaceutical composition comprising a protein kinase C(PKC) activator or 4-methylcatechol acetic acid (MCBA) and a pharmaceutically acceptable carrier effective to treat at least one symptom of head trauma.

In one embodiment, the PKC activator is FGF-18, a macrocyclic lactone, a benzolactam, a pyrrolidinone, or a combination thereof. In a preferred embodiment, the macrocyclic lactone is a bryostatin or neristatin. In another embodiment, the neristatin is neristatin-1. In another embodiment, the bryostatin is bryostatin-1, 2, 3, 4, 5, 6, 7, 8, 9, 10, 11, 12, 13, 14, 15, 16, 17 or 18. More preferably, the bryostatin is bryostatin-1.

In another preferred embodiment, the pharmaceutical composition comprises 4-methylcatechol acetic acid (MCBA), other derivatives of methylcatechol, or a brain derived neurotrophic factor. MCBA and other derivatives of methylcatechol activate or upregulate nerve growth factor (NGF), brain derived neurotrophic factor (BDNF) or other neurotrophic factors. NGF activates, upregulates or enhances the activity of PKC which in turn upregulates, activates or enhances NGF.

In one embodiment, administration of the pharmaceutical compositions of the present invention is initiated within 1, 2, 3, 4, 5, 6, 7, 8, 9, 10, 11, 12, 13, or 14 days of said head trauma. In another embodiment, said administration is initiated between 1 and 2 days, 1 and 3 days, 1 and 4 days, 1 and 5 or 1 and 7 days of said head trauma. In another embodiment, the administration of the pharmaceutical compositions of the present invention is initiated within 1, 2, 3, 4, 5, 6, 7, 8, 9, 10, 11, 12, 13, 14, 15, 16, 17, 18, 19, 20, 21, 22, 23, or 24 hours of said head trauma. In yet another embodiment, the administration of the pharmaceutical compositions of the present invention is initiated between 1 and 3, 1 and 5, 1 and 10, 1 and 24, 3 and 5, 3 and 10, 3 and 24, 5 and 10, 5 and 24, or 10 and 24 hours after said head trauma. In yet another embodiment, the administration of the pharmaceutical compositions of the present invention is initiated after 3, 4, 5, 6, 7, 8, 9, 10, 11, 12, 13, 14, 15, 16, 17, 18, 19, 20, 21, 22, 23, or 24 hours after said head trauma. In yet another embodiment, the administration of the pharmaceutical compositions of the present invention is initiated after 1, 2, 3, 4, 5, 6, 7, 8, 9, 10, 11, 12, 13, 14, 15, 16, 17, 18, 19, 20, or 21 days after said head trauma.

In one embodiment, treatment comprising the administration of the pharmaceutical compositions of the present invention is continued for a duration of about 1, 2, 3, 4, 5, 6, 7, 8, 9, 10, 11, or 12 weeks.

DETAILED DESCRIPTION OF THE INVENTION

A. Definitions

Figure 1:
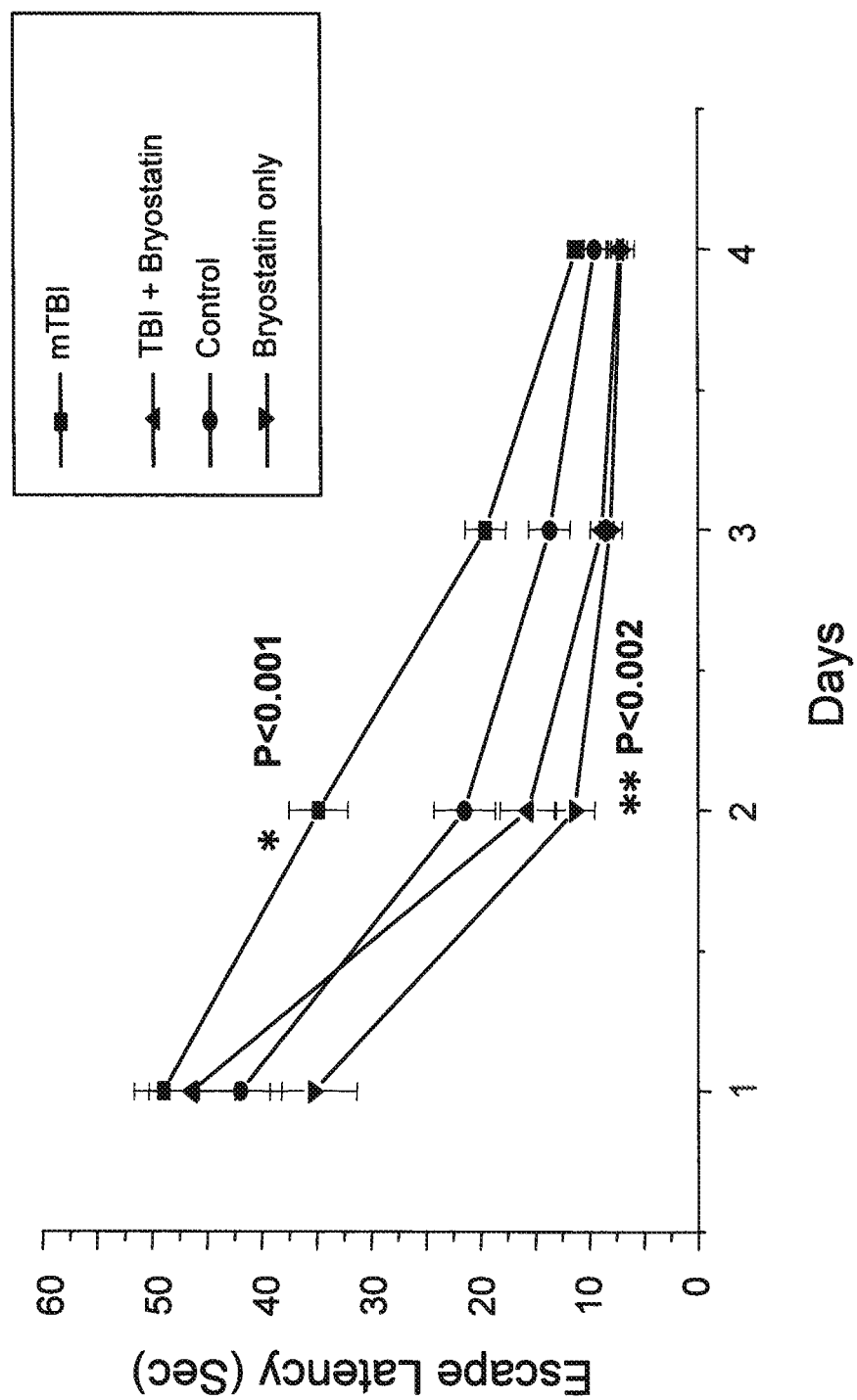
FIG. 1 depicts the escape latencies of mice after minimal traumatic brain injury (TBI)(30 g) followed by 30 ug/kg bryostatin injected intraperitoneally.

As used herein, "administration" of a composition includes any route of administration, including oral subcutaneous, intraperitoneal, and intramuscular.

As used herein, "an effective amount" is an amount sufficient to reduce one or more symptoms associated with a head trauma.

As used herein, "protein kinase C activator" or "PKC activator" means a substance that increases the rate of the reaction catalyzed by protein kinase C by binding to the protein kinase C.

As used herein, the term "subject" means a mammal.

As used herein, the term "pharmaceutically acceptable carrier" means a chemical composition with which the active ingredient may be combined and which, following the combination, can be used to administer the active ingredient to a subject. As used herein, the term "physiologically acceptable" ester or salt means an ester or salt form of the active ingredient which is compatible with any other ingredients of the pharmaceutical composition, which is not deleterious to the subject to which the composition is to be administered.

As used herein, "pharmaceutically acceptable carrier" also includes, but is not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

Despite progress toward the development of new therapeutic agents and availability of several animal models, there is still a pressing need for improved animal models for screening B. Animal Models of Learning and Memory The area of memory and learning impairment is rich in animal models that are able to demonstrate different features of memory and learning processes. (See, for example, Hollister, L. E., 1990, Pharmacopsychiat., 23, (Suppl II) 33-36). The available animal models of memory loss and impaired learning involve measuring the ability of animals to remember a discrete event. These tests include the Morris Water Maze and the passive avoidance procedure. In the Morris Water Maze, animals are allowed to swim in a tank divided into four quadrants, only one of which has a safety platform beneath the water. The platform is removed and the animals are tested for how long they search the correct quadrant verse the incorrect quadrants. In the passive avoidance procedure the animal remembers the distinctive environment in which a mild electric shock is delivered and avoids it on a second occasion. A variant of the passive avoidance procedure makes use of a rodent's preference for dark enclosed environments over light open ones. Further discussion can be found in Crawley, J. N., 1981, Pharmacol. Biochem. Behav., 15, 695-699; Costall, B. et al, 1987, Neuropharmacol., 26, 195-200; Costall, B. et al., 1989, Pharmacol. Biochem. Behav., 32, 777-785; Barnes, J. M. et al., 1989, Br. J. Pharmacol., 98 (Suppl) 693P; Barnes, J. M. et al., 1990, Pharmacol. Biochem. Behav., 35, 955-962.

C. Protein Kinase C (PKC)

The PKC gene family consists presently of 11 genes which are divided into four subgroups: 1) classical PKC$\alpha$, $\beta_1$, $\beta_2$ ($\beta_1$ and $\beta_2$ are alternatively spliced forms of the same gene) and $\gamma$, 2) novel PKC$\delta$, $\epsilon$, $\eta$, and $\theta$, 3) atypical PKC$\zeta$, $\lambda$, $\eta$ and $\iota$ and 4) PKC $\mu$. PKC $\mu$ resembles the novel PKC isoforms but differs by having a putative transmembrane domain (reviewed by Blohe et al. (1994) *Cancer Metast. Rev.* 13: 411; Ilug et al. (1993) *Biochem J.* 291: 329; Kikkawa et al. (1989) *Ann. Rev. Biochem.* 58: 31). The $\alpha$, $\beta_1$, $\beta_2$ and $\gamma$ isoforms are $C^{2+}$, phospholipid and diacylglycerol-dependent and represent the classical isoforms of PKC, whereas the other isoforms are activated by phospholipid and diacylglycerol but are not dependent on $Ca^{2+}$. All isoforms encompass 5 variable (V1-V5) regions, and the $\alpha$, $\beta$, and $\gamma$ isoforms contain four (C1-C4) structural domains which are highly conserved. All isoforms except PKC $\alpha$, $\beta$ and $\gamma$ lack the C2 domain, the $\lambda$ $\eta$ and isoforms also lack nine of two cysteine-rich zinc finger domains in C1 to which diacylglycerol binds. The C1 domain also contains the pseudosubstrate sequence which is highly conserved among all isoforms, and which serves an autoregulartory function by blocking the substrate-binding site to produce an inactive conformation of the enzyme (House et al. (1987) *Science* 238, 1726).

Because of these structural features, diverse PKC isoforms are thought to have highly specialized roles in signal transduction in response to physiological stimuli (Nishizuka (1989) *Cancer* 10: 1892), as well as in neoplastic transformation and differentiation (Glazer (1994) *Protein Kinase C*, J. F. Kuo, ed., Oxford U. Press at pages 171-198). For a discussion of known PKC modulators see PCT/US97/08141, U.S. Pat. Nos. 5,652,232; 6,080,784; 5,891,906; 5,962,498; 5,955,501; 5,891,870 and 5,962,504 (each incorporated herein by reference in its entirety).

There is increasing evidence that the individual PKC isozymes play different, sometimes opposing, roles in biological processes, providing two directions for pharmacological exploitation. One is the design of specific (preferably, isozyme specific) inhibitors of PKC. This approach is complicated by the act that the catalytic domain is not the domain primarily responsible for the isotype specificity of PKC. The other approach is to develop isozyme-selective, regulatory site-directed PKC activators. These may provide a way to override the effect of other signal transduction pathways with opposite biological effects. Alternatively, by inducing down-regulation of PKC after acute activation, PKC activators may cause long term antagonism. Bryostatin is currently in clinical trials as an anti-cancer agent. The bryostatins are known to bind to the regulatory domain of PKC and to activate the enzyme. Bryostatins are examples of isozyme-selective activators of PKC. (see for example WO 97/43268; incorporated herein by reference in its entirety). For a discussion of known PKC modulators see PCT/US97/08141, U.S. Pat. Nos. 5,652,232; 6,043,270; 6,080,784; 5,891,906; 5,962,498; 5,955,501; 5,891,870 and 5,962,504 (each of which is incorporated herein by reference in its entirety).

Several classes of PKC activators have been identified. Phorbol esters, however, are not suitable compounds for eventual drug development because of their tumor promotion activity, (Ibarreta et al. (1999) *Neuro Report* 10(5&6): 1035-40). Of particular interest are macrocyclic lactones (i.e. bryostatin class and neristatin class) that act to stimulate PKC. Of the bryostatin class compounds., bryostatin-1 has been shown to activate PKC and proven to be devoid of tumor promotion activity. Bryostatin-1, as a PKC activator, is also particularly useful since the dose response curve of bryostatin-1 is biphasic. Additionally, bryostatin-1 demonstrates differential regulation of PKC isozymes, including PKC$\alpha$, PKC$\delta$ and PKC$\epsilon$. Bryostatin-1 has undergone toxicity and safety studies in animals and humans and is actively investigated as an anti-cancer agent. Bryostatin-1's use in the studies has determined that the main adverse reaction in humans is myalgia. One example of an effective dose is 20 or 30 µg/kg per dose by intraperitoneal injection.

Macrocyclic lactones, and particularly bryostatin-1, are described in U.S. Pat. No. 4,560,774 (incorporated herein by reference in its entirety). Macrocyclic lactones and their derivatives are described elsewhere in U.S. Pat. No. 6,187,568, U.S. Pat. No. 6,043,270, U.S. Pat. No. 5,393,897, U.S. Pat. No. 5,072,004, U.S. Pat. No. 5,196,447, U.S. Pat. No. 4,833,257, and U.S. Pat. No. 4,611,066 (each incorporated herein by reference in its entirety). The above patents describe various compounds and various uses for macrocyclic lactones including their use as an anti-inflammatory or anti-tumor agent. (Szallasi et al. (1994) *Journal of Biological Chemistry* 269(3): 2118-24; Zhang et al. (1996) *Caner Research* 56: 802-808; Hennings et al. (1987) *Carcinogenesis* 8(9): 1343-1346; Varterasian et al. (2000) *Clinical Cancer Research* 6: 825-828; Mutter et al. (2000) *Bioorganic & Medicinal Chemistry* 8: 1841-1860)(each incorporated herein by reference in its entirety).

As will also be appreciated by one of ordinary skill in the art, macrocyclic lactone compounds and their derivatives, particularly the bryostatin class, are amenable to combinatorial synthetic techniques and thus libraries of the compounds can be generated to optimize pharmacological parameters, including, but not limited to efficacy and safety of the compositions. Additionally, these libraries can be assayed to determine those members that preferably modulate $\alpha$-secretase and/or PKC.

Combinatorial libraries high throughput screening of natural products and fermentation broths has resulted in the discovery of several new drugs. At present, generation and screening of chemical diversity is being utilized extensively as a major technique for the discovery of lead compounds, and this is certainly a major fundamental advance in the area of drug discovery. Additionally, even after a "lead" compound has been identified, combinatorial techniques provide for a valuable tool for the optimization of desired biological activity. As will be appreciated, the subject reaction readily lend themselves to the creation of combinatorial libraries of compounds for the screening of pharmaceutical, or other biological or medically-related activity or material-related qualities. A combinatorial library for the purposes of the present invention is a mixture of chemically related compounds, which may be screened together for a desired property; said libraries may be in solution or covalently linked to a solid support. The preparation of many related compounds in a single reaction greatly reduces and simplifies the number of screening processes that need to be carried out. Screening for the appropriate biological property may be done by conventional methods. Thus, the present invention also provides methods for determining the ability of one or more inventive compounds to bind to effectively modulate $\alpha$-secretase and/or PKC.

A variety of techniques are available in the art for generating combinatorial libraries described below, but it will be understood that the present invention is not intended to be limited by the foregoing examples and descriptions. (See, for example, Blondelle et al. (1995) *Trends Anal. Chem.* 14: 83; U.S. Pat. Nos. 5,359,115; 5,362,899; U.S. Pat. No. 5,288,514: PCT publication WO 94/08051; Chen et al. (1994) *JACCS* 1 6:266 1: Kerr et al. (1993) *JACCS* 1 1 5:252; PCT publications WO92/10092, WO93/09668; WO91/07087; and WO93/20242; each of which is incorporated herein by reference). Accordingly, a variety of libraries on the order of about 16 to 1,000,000 or more diversomers can be synthesized and screened for a particular activity or property.

Analogs of bryostatin, commonly referred to as bryologs, are one particular class of PKC activators that are suitable for use in the methods of the present invention. The following Table summarizes structural characteristics of several bryologs, demonstrating that bryologs vary greatly in their affinity for PKC (from 0.25 nM to 10 μM). Structurally, they are all similar. While bryostatin-1 has two pyran rings and one 6-membered cyclic acetal, in most bryologs one of the pyrans of bryostatin-1 is replaced with a second 6-membered acetal ring. This modification reduces the stability of bryologs, relative to bryostatin-1, for example, in both strong acid or base, but has little significance at physiological pH. Bryologs also have a lower molecular weight (ranging from about 600 to 755), as compared to bryostatin-1 (988), a property which facilitates transport across the blood-brain barrier.

| Name | PKC Affin (nM) | MW | Description |
|---|---|---|---|
| Bryostatin 1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals + macrocycle |
| Analog 9 | 10000 | 599 | 2 cyclic acetals |

Analog 1 (Wender et al. (2004) *Curr Drug Discov Technol.* 1:1; Wender et al. (1998) *Proc Natl Acad Sci USA* 95: 6624; Wender et al. (2002) *Am Chem Soc.* 124: 13648 (each incorporated herein by reference in their entireties)) possesses the highest affinity for PKC. This bryolog is about 100 times more potent than bryostatin-1. Only Analog 1 exhibits a higher affinity for PKC than bryostatin. Analog 2, which lacks the A ring of bryostatin-1 is the simplest analog that maintains high affinity for PKC. In addition to the active bryologs, Analog 7d, which is acetylated at position 26, has virtually no affinity for PKC.

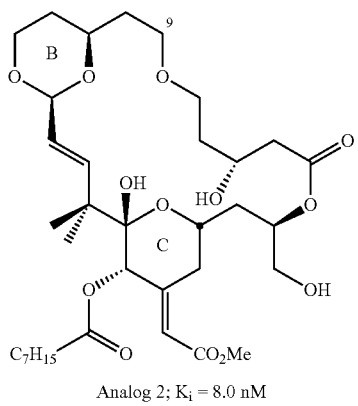

Analog 2; K$_i$ = 8.0 nM

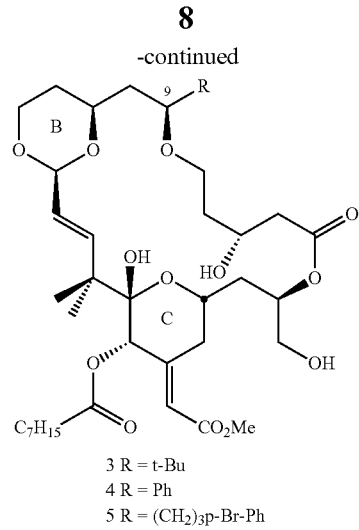

3 R = t-Bu
4 R = Ph
5 R = (CH$_2$)$_3$p-Br-Ph

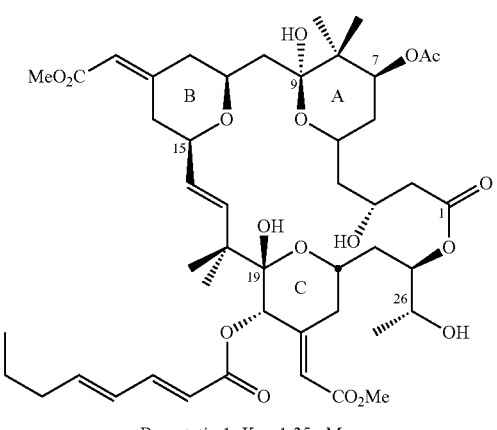

Bryostatin 1; K$_i$ = 1.35 nM

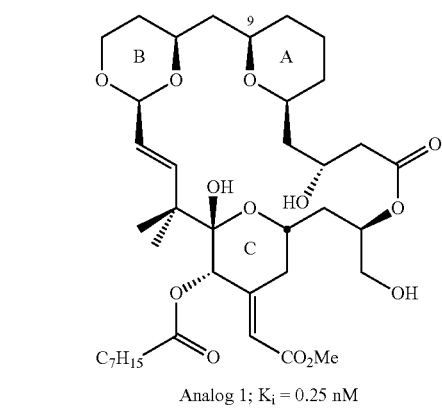

Analog 1; K$_i$ = 0.25 nM

B-ring bryologs are also suitable for use in the methods of the present invention. These synthetic bryologs have affinities in the low nanomolar range (Wender et al. (2006) *Org Lett.* 8: 5299 (incorporated herein by reference in its entirety)). The B-ring bryologs have the advantage of being completely synthetic, and do not require purification from a natural source.

PKC binding affinities for B-ring bryologs

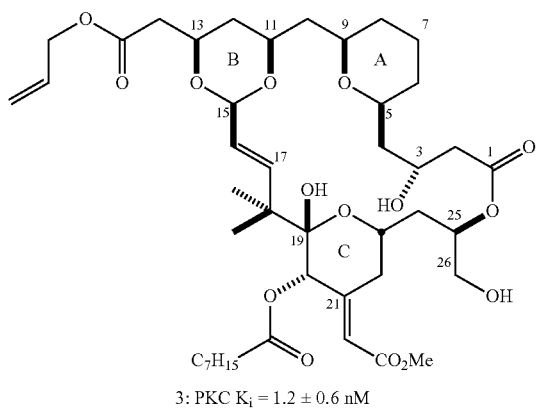

3: PKC $K_i$ = 1.2 ± 0.6 nM

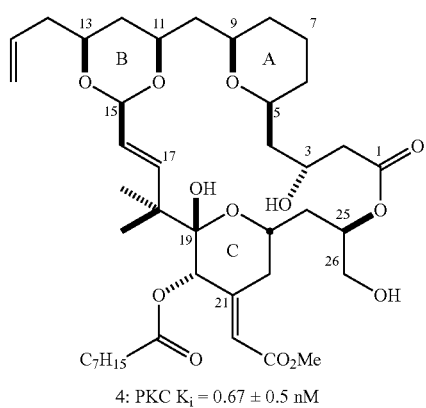

4: PKC $K_i$ = 0.67 ± 0.5 nM

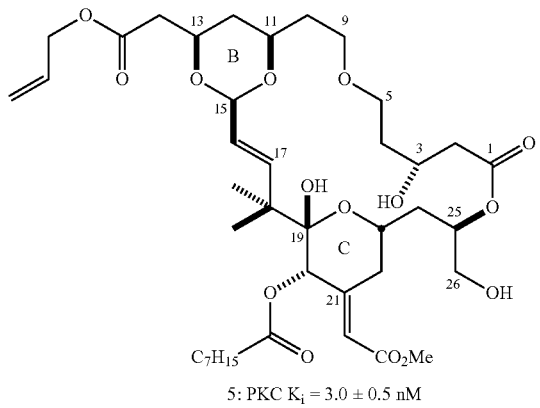

5: PKC $K_i$ = 3.0 ± 0.5 nM

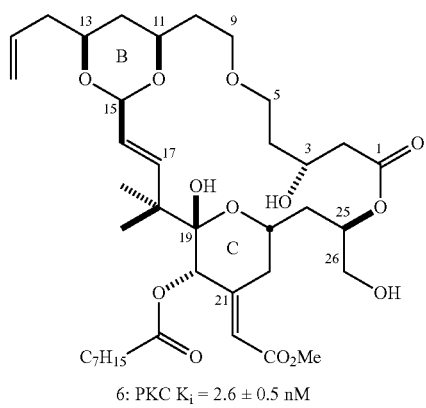

6: PKC $K_i$ = 2.6 ± 0.5 nM

A third class of suitable bryostatin analogs is the A-ring bryologs. These bryologs have slightly lower affinity for PKC than bryostatin I (6.5, 2.3, and 1.9 nM for bryologs 3, 4, and 5, respectively) but have a lower molecular weight.

A number of derivatives of diacylglycerol (DAG) bind to and activate protein kinase C (Niedel et al. (1983) Proc. Natl. Acad. Sci. USA 80: 36; Mori et al. (1982) J. Biochem (Tokyo) 91: 427; Kaibuchi et al. (1983) J. Biol. Chem. 258: 6701). However, DAG and DAG derivatives are of limited value as drugs. Activation of PKC by diacylglycerols is transient, because they are rapidly metabolized by diacylglycerol kinase and lipase (Bishop et al. (1986) J. Biol. Chem. 261: 6993; Chung et al. (1993) Am. J. Physiol. 265: C927; incorporated herein by reference in their entireties). The fatty acid substitution determines the strength of activation. Diacylglycerols having an unsaturated fatty acid are most active. The stereoisomeric configuration is also critical. Fatty acids with a 1,2-sn configuration are active, while 2,3-sn-diacylglycerols and 1,3-diacylglycerols do not bind to PKC. Cis-unsaturated fatty acids are synergistic with diacylglycerols. In one embodiment of the present invention, the term "PKC activator" expressly excludes DAG or DAG derivatives, such as phorbol esters.

Isoprenoids are PKC activators suitable for use in the methods of the present invention. Farnesyl thiotriazole, for example, is a synthetic isoprenoid that activates PKC with a Kd of 2.5 µM. Farnesyl thiotriazole, for example, is equipotent with dioleoylglycerol (Gilbert et al. (1995) Biochemistry 34: 3916; incorporated herein by reference in its entirety), but does not possess hydrolyzable esters of fatty acids. Farnesyl thiotriazole and related compounds represent a stable, persistent PKC activator. Because of its low MW (305.5) and absence of charged groups, farnesyl thiotriazole would readily cross the blood-brain barrier.

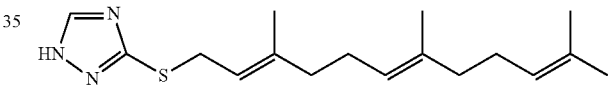

Octylindolactam V is a non-phorbol protein kinase C activator related to teleocidin. The advantages of octylindolactam V, specifically the (−)-enantiomer, include greater metabolic stability, high potency (Fujiki et al. (1987) Adv. Cancer Res. 49: 223; Collins et al. (1982) Biochem. Biophys. Res. Commun. 104: 1159; each incorporated herein by reference in its entirety)($EC_{50}$=29 nM) and low molecular weight that facilitates transport across the blood brain barrier.

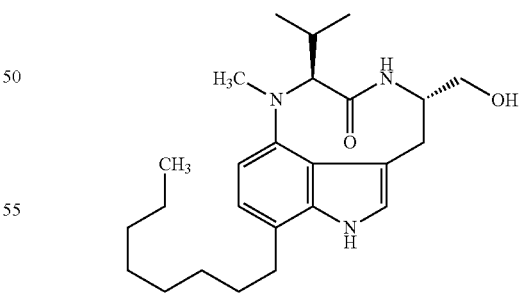

Gnidimacrin is a daphnane-type diterpene that displays potent antitumor activity at concentrations of 0.1-1 nM against murine leukemias and solid tumors. It acts as a PKC activator at a concentration of ≈3 nM in K562 cells, and regulates cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to bryostatin, but somewhat smaller (MW=774.9).

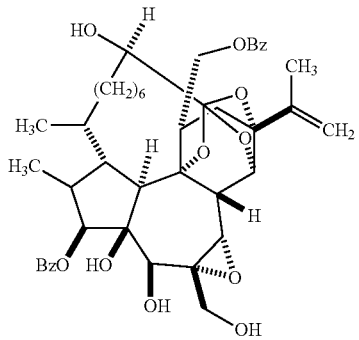

Iripallidal is a bicyclic triterpenoid isolated from Iris pallida. Iripallidal displays anti-proliferative activity in a NCI 60 cell line screen with GI50 (concentration required to inhibit growth by 50%) values from micromolar to nanomolar range. It binds to PKCα with high affinity (Ki=75.6 nM). It induces phosphorylation of ERK1/2 in a RasGRP3-dependent manner. M.W. 486.7. Iripallidal is only about half the size of bryostatin and lacks charged groups.

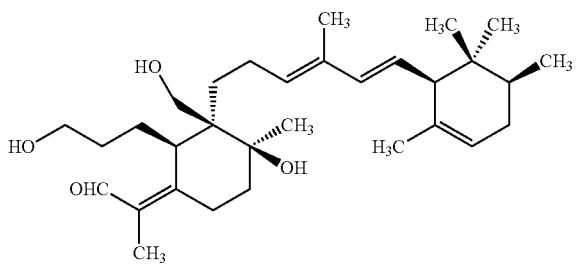

Ingenol [43] is a diterpenoid related to phorbol but possesses much less toxicity. It is derived from the milkweed plant Euphorbia peplus. Ingenol 3,20-dibenzoate, for example, competes with [3H]phorbol dibutyrate for binding to PKC (Ki for binding=240 nM) (Winkler et al. (1995) J. Org. Chem. 60: 1381; incorporated herein by reference). Ingenol-3-angelate possesses antitumor activity against squamous cell carcinoma and melanoma when used topically (Ogboume et al. (2007) Anticancer Drugs. 18: 357; incorporated herein by reference).

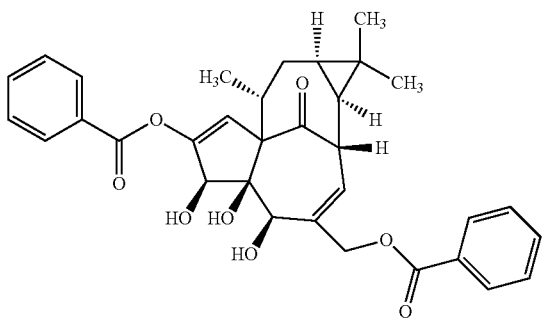 [SMILES: C[C@@H]1C[C@@H]2[C@H]([C@@H]3C=C(COC(=O)c4ccccc4)[C@@H](O)[C@]4(O)[C@@H](O)C(OC(=O)c5ccccc5)=CC14C3=O)C2(C)C]

Napthalenesulfonamides, including N-(n-heptyl)-5-chloro-1-naphthalenesulfonamide (SC-10) and N-(6-Phenylhexyl)-5-chloro-1-naphthalenesulfonamide, are members of another class of PKC activators. SC-10 activates PKC in a calcium-dependent manner, using a mechanism similar to that of phosphatidylserine (Ito et al. (1986) Biochemistry 25: 4179; incorporated herein by reference). Naphthalenesulfonamides act by a different mechanism from bryostatin and would be expected to show a synergistic effect with bryostatin or a member of another class of PKC activators. Structurally, naphthalenesulfonamides are similar to the calmodulin (CaM) antagonist W-7, but are reported to have no effect on CaM kinase.

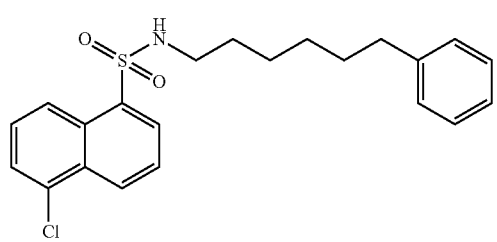 [SMILES: O=S(=O)(NCCCCCCc1ccccc1)c1cccc2c(Cl)cccc12]

The linoleic acid derivative DCP-LA (2-[(2-pentylcyclopropyl)methyl]cyclopropaneoctanoic acid) is one of the few known isoform-specific activators of PKC known. DCP-LA selectively activates PKCε with a maximal effect at 100 nM. (Kanno et al. (2006) J. Lipid Res. 47: 1146). Like SC-10, DCP-LA interacts with the phosphatidylserine binding site of PKC, instead of the diacylglycerol binding site.

An alternative approach to activating PKC directly is to increase the levels of the endogenous activator, diacylglycerol. Diacylglycerol kinase inhibitors such as 6-(2-(4-[(4-fluorophenyl)phenylmethylene]-1-piperidinyl)ethyl)-7-methyl-5H-thiazolo[3,2-a]pyrimidin-5-one (R59022) and [3-[2-[4-(bis-(4-fluorophenyl)methylene]piperidin-1-yl) ethyl]-2,3-dihydro-2-thioxo-4(1H)-quinazolinone (R59949) enhance the levels of the endogenous ligand diacylglycerol, thereby producing activation of PKC (Meinhardt et al. (2002) Anti-Cancer Drugs 13: 725).

Growth factor activators, such as the 4-methyl catechol derivatives, such as 4-methylcatechol acetic acid (MCBA), that stimulate the synthesis and/or activation of growth factors such as NGF and BDNF, also activate PKC as well as convergent pathways responsible for synaptogenesis and/or neuritic branching.

All books, articles, patents or other publications and references are hereby incorporated by reference in their entireties. Reference to any compound herein includes the racemate as well as the single enantiomers

EXAMPLES

The following Examples serve to further illustrate the present invention and are not to be construed as limiting its scope in any way.

Example 1

Animal Model of Head Trauma

Minimal traumatic brain injury (TBI) was produced in mice by a concussive event using a 30 g mass. One hour post trauma, the mice received 20 or 30 μg bryostatin per kg doses by intraperitoneal injection. The injections were repeated twice weekly for a total of 5 treatments. The effects on learning and memory of bryostatin treatment in treated animals was tested in the Morris Water Maze.

Example 2

Morris Water Maze

In the Morris Water Maze, animals were allowed to swim in a tank divided into four quadrants, only one of which had a safety platform beneath the water. The platform was removed and the animals were tested for how long they searched the correct quadrant versus the incorrect quadrants. In the passive avoidance procedure the animal remembers the distinctive environment in which a mild electric shock is delivered and avoids it on a second occasion.

Example 3

Bryostatin (30 ug/kg) and Treatment of Minimal TBI

Minimal traumatic brain injury (TBI) was produced in mice by a concussive event using a 30 g mass. One hour post trauma, the mice received 30 μg bryostatin per kg doses by intraperitoneal injection. The injections were repeated twice weekly for a total of 5 treatments. The escape latencies in a Morris Water Maze of mice treated with bryostatin after minimal TBI were compared to animals with minimal TBI, control animals receiving no TBI or bryostatin, and animals receiving bryostatin only. The results are shown in FIG. 1.

Example 4

Bryostatin (20 ug/kg) and Treatment of Minimal TBI

Figure 2:
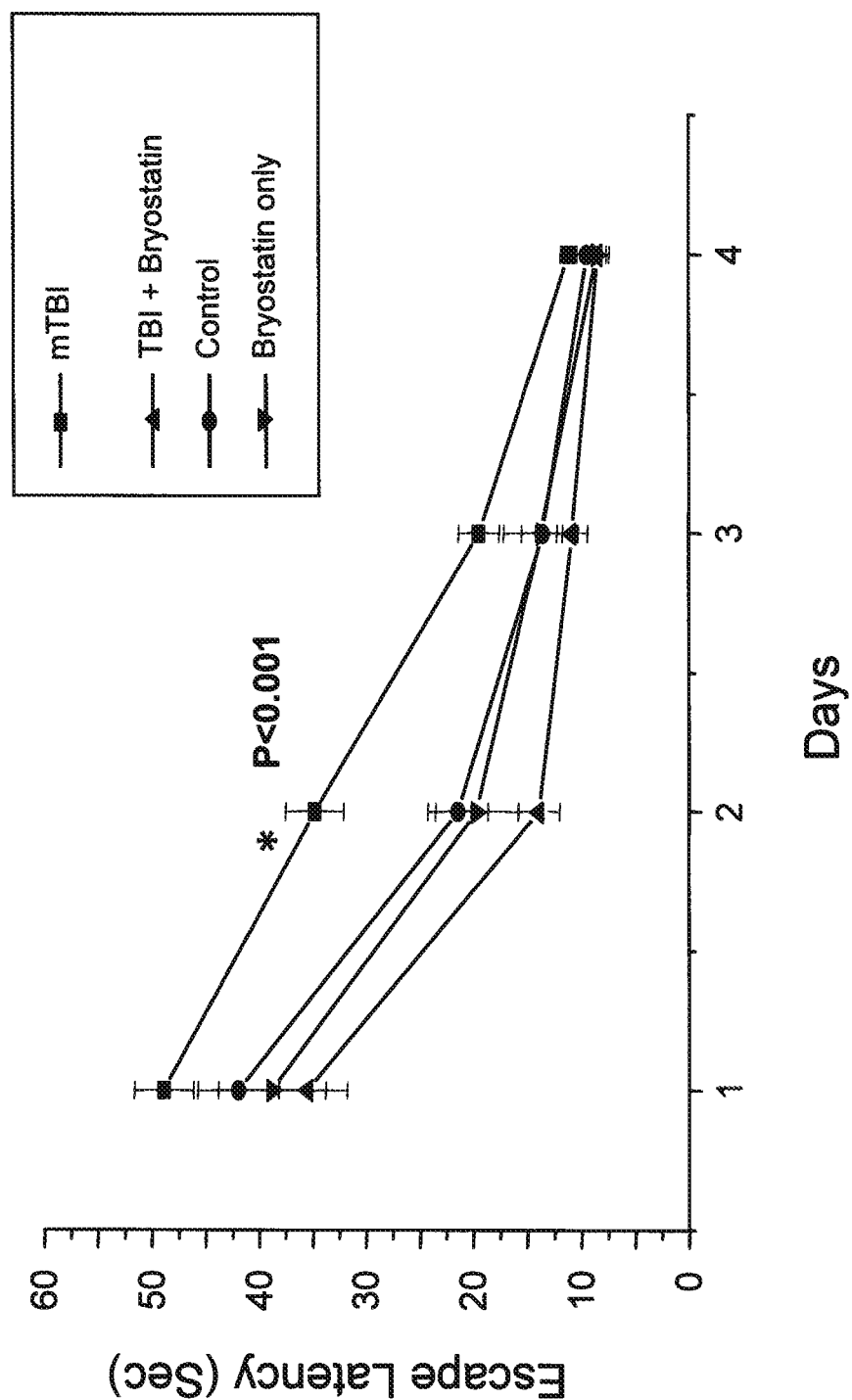
FIG. 2 depicts the escape latencies of mice after minimal traumatic brain injury (TBI) (30 g):followed by 20 ug/kg bryostatin injected intraperitoneally.
Figure 3:
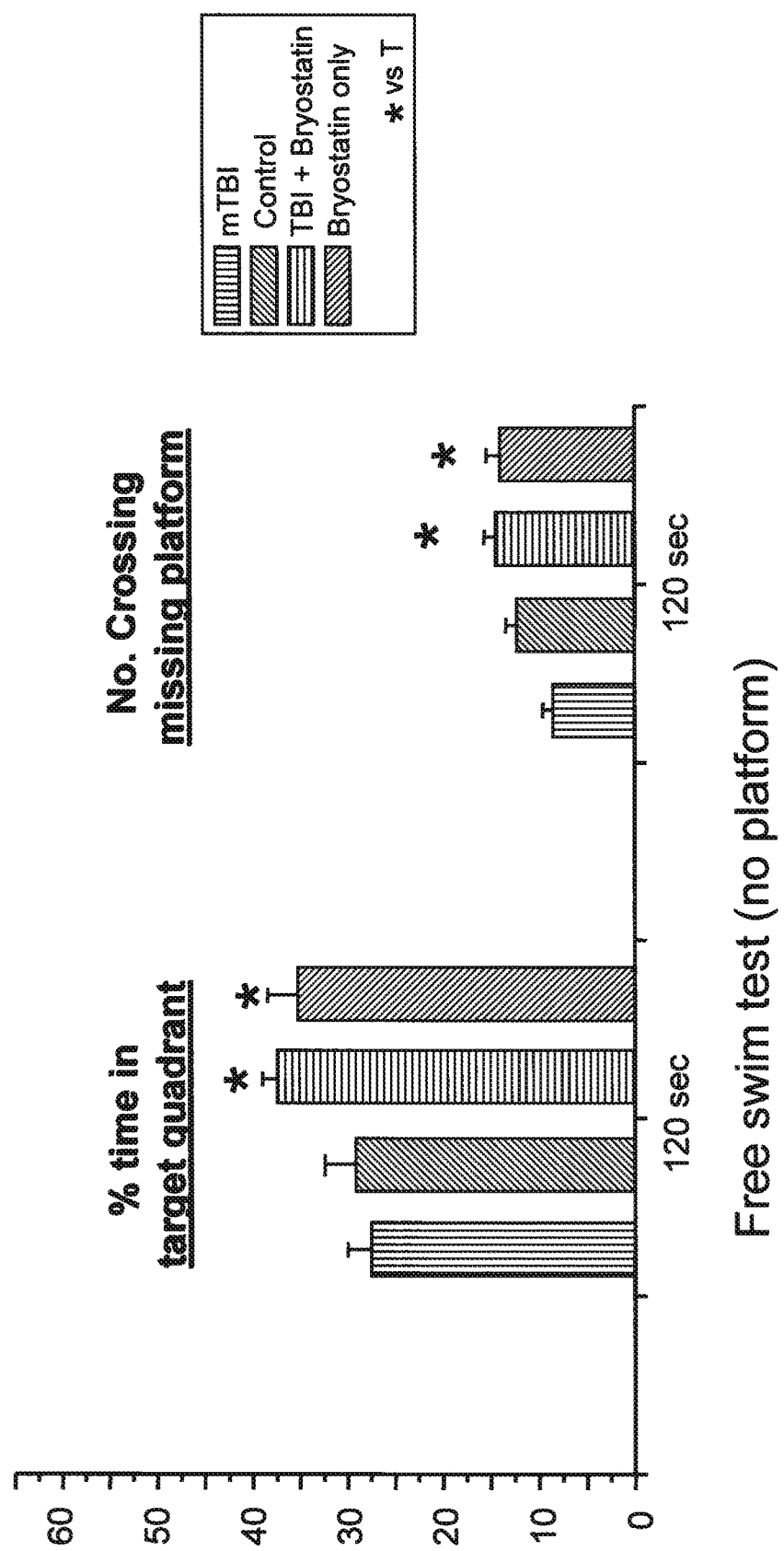
FIG. 3 depicts memory retention in mice after minimal TBI (30 g) followed by 20 ug/kg bryostatin injected intraperitoneally.

Minimal traumatic brain injury (TBI) was produced in mice by a concussive event using a 30 g mass. One hour post trauma, the mice received 20 μg bryostatin per kg doses by intraperitoneal injection. The injections were repeated twice weekly for a total of 5 treatments. The escape latencies in a Morris Water Maze of mice treated with bryostatin after minimal TBI were compared to animals with minimal TBI, control animals receiving no TBI or bryostatin, and animals receiving bryostatin only. The results are shown in FIG. 2. The memory retention of each treatment or control group is tabulated in FIG. 3.

We claim:

1. A method of treating post-head trauma memory deficits resulting from brain injury comprising the steps of identifying a human subject having suffered a brain injury resulting from head trauma and administering to said subject an amount of a pharmaceutical composition comprising a protein kinase C (PKC) activator, and a pharmaceutically acceptable carrier effective to treat at least one symptom of head trauma, wherein the PKC activator is chosen from

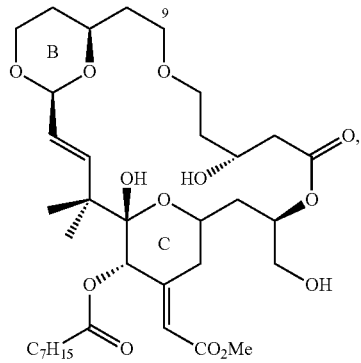

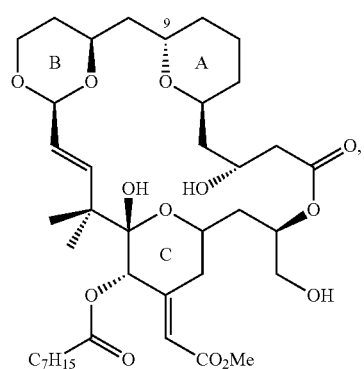

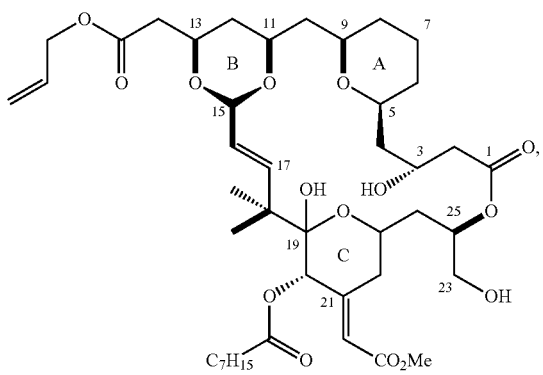

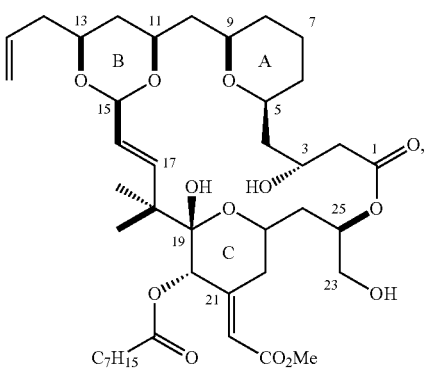

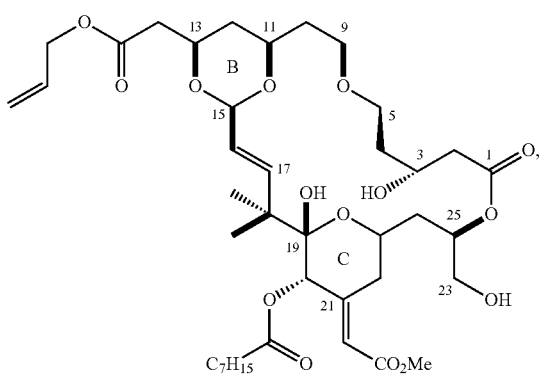

-continued

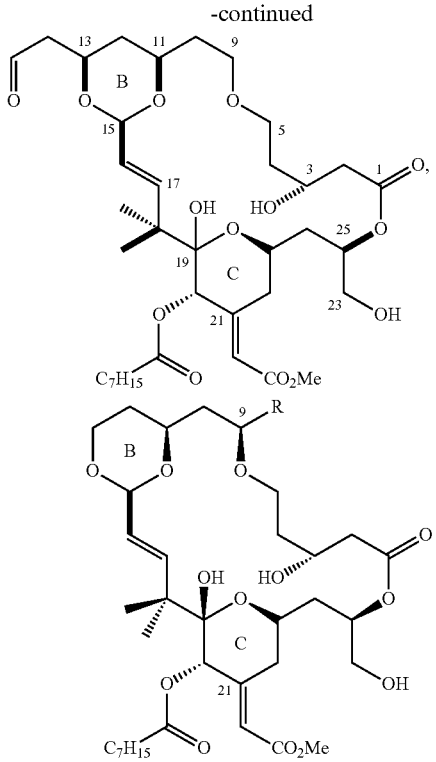

and wherein R is t-Bu, Ph, or $(CH_2)_3$p-Br-Ph, and
wherein the administration is initiated within 3 days of the head trauma and is continued for a duration in a range from about 1 week to about 12 weeks.

2. The method of claim 1, wherein the PKC activator has a molecular weight from about 600 to 755 and an affinity for PKC from about 0.25 nM to 10 μM.

3. The method of claim 1, wherein said administration is initiated within 1 day of said head trauma.

4. The method of claim 1, wherein said administration is initiated within 2 days of said head trauma.

5. The method of claim 1, wherein said administration is initiated within 3 days of said head trauma.

6. The method of claim 1, wherein said administration is initiated between 1 and 2 days of said head trauma.

7. The method of claim 1, wherein said administration is initiated between 1 and 3 days of said head trauma.

8. The method of claim 1, wherein the treatment is continued for a duration of 1 week.

9. The method of claim 1, wherein the treatment is continued for a duration of 2 weeks.

10. The method of claim 1, wherein the treatment is continued for a duration of 3 weeks.

11. The method of claim 1, wherein the treatment is continued for a duration of 4 weeks.

12. The method of claim 1, wherein the treatment is continued for a duration of 6 weeks.

\* \* \* \* \*